(12) United States Patent
Beck et al.

(10) Patent No.: US 9,133,254 B2
(45) Date of Patent: *Sep. 15, 2015

(54) PROTECTIVE, HYDROCOLLOID FOR ACTIVE INGREDIENTS

(71) Applicant: DSM IP ASSETS B.V., Heerlen (NL)

(72) Inventors: Markus Beck, Lorrach (DE); Navagnana S. Hettiarachchy, Fayetteville, AR (US); Bruno H. F. Leuenberger, Rheinfelden (CH); Ilankovan Paraman, Ames, IA (US); Christian Schaefer, Rheinfelden (CH); Gerhard Wagner, Wehr (DE)

(73) Assignee: DSM IP ASSETS B.V., Heerlen (NL)

( * ) Notice: Subject to any disclaimer, the term of this patent is extended or adjusted under 35 U.S.C. 154(b) by 190 days.

This patent is subject to a terminal disclaimer.

(21) Appl. No.: 13/762,640

(22) Filed: Feb. 8, 2013

(65) Prior Publication Data

US 2014/0057999 A1    Feb. 27, 2014

Related U.S. Application Data

(62) Division of application No. 12/095,927, filed as application No. PCT/EP2006/011873 on Dec. 8, 2006, now abandoned.

(60) Provisional application No. 60/748,192, filed on Dec. 8, 2005.

(51) Int. Cl.
| | |
|---|---|
| C07K 1/14 | (2006.01) |
| C07K 1/107 | (2006.01) |
| C07K 14/415 | (2006.01) |
| A23J 1/12 | (2006.01) |
| A23J 3/14 | (2006.01) |
| A23J 3/34 | (2006.01) |
| A23K 1/00 | (2006.01) |
| A23K 1/16 | (2006.01) |
| A23L 1/00 | (2006.01) |
| A23L 1/10 | (2006.01) |
| A23L 1/275 | (2006.01) |
| A23L 1/303 | (2006.01) |
| A61K 47/42 | (2006.01) |
| C12P 21/06 | (2006.01) |
| A61K 38/00 | (2006.01) |

(52) U.S. Cl.
CPC .............. *C07K 14/415* (2013.01); *A23J 1/12* (2013.01); *A23J 3/14* (2013.01); *A23J 3/34* (2013.01); *A23K 1/001* (2013.01); *A23K 1/1603* (2013.01); *A23K 1/1606* (2013.01); *A23L 1/0035* (2013.01); *A23L 1/1016* (2013.01); *A23L 1/1041* (2013.01); *A23L 1/2753* (2013.01); *A23L 1/303* (2013.01); *A61K 47/42* (2013.01); *C12P 21/06* (2013.01); *C12Y 304/00* (2013.01)

(58) Field of Classification Search
None
See application file for complete search history.

(56) References Cited

U.S. PATENT DOCUMENTS

| | | | |
|---|---|---|---|
| 3,806,603 A | 4/1974 | Gaunt et al. | |
| 6,143,558 A | 11/2000 | Kopelman et al. | |
| 2003/0172403 A1 | 9/2003 | Huang et al. | |
| 2004/0022926 A1 | 2/2004 | Bartocci et al. | |
| 2004/0111766 A1 | 6/2004 | Huang et al. | |

FOREIGN PATENT DOCUMENTS

| | | |
|---|---|---|
| EP | 1 070 457 | 1/2001 |
| EP | 1 656 970 | 5/2006 |
| ES | 2 161 640 | 12/2001 |
| FR | 2 825 925 | 12/2002 |
| WO | 2005/013708 | 2/2005 |
| WO | 2005/123545 | 12/2005 |

OTHER PUBLICATIONS

Anderson et al. (2001) Physicochemical properties of pronase-treated rice glutelin, JAOCS (J. Am. Oil Chem. Society), vol. 78, No. 1, pahes 1-6.*
International Search Report dated May 21, 2007.
Written Opinion of the International Searching Authority dated May 21, 2007.
Souci et al.: "Food composition and nutrition tables 1986/1987," 1986, Deutsche Forschungsanhalt Fur Lebensmittelchemie, Garsching B. Munchen, pp. 498-501, XP002424064.
Anonyme: "Bilberry and Bio-repair Complex Overnight Rebalancing Cream," Internet Citation, Jun. 30, 2004, http://web.archive.org/web/20040630143628 www.ulta.com/control/product/category_id=161/product_id=2085306>, XP002338934.
Anonymous: "Riz au lait saveur vanilla—Carrefour—Liste des ingredients" Internet Article, www.ooshop.com, XP002424062.
Anonymous: "Riz au lait saveur vanilla—La Laitiere" Internet Article, www.ooshop.com, XP002430121.
Guerinot Mary Lou: "The green revolution strikes gold" Science, vol. 287, No. 5451, Jan. 14, 2000, pp. 241-243, XP002424063.
Tatsuya Morita et al.: "Mass Production Method for Rice Protein Isolate and Nutritional Evalation," Journal of Food Science, Institute of Food Technologists, Chicago, Illinois, vol. 58, No. 6, Nov. 1, 1993, pp. 1393-1396, 1406, XP000418015.

(Continued)

*Primary Examiner* — Manjunath Rao
*Assistant Examiner* — Samuel Liu
(74) *Attorney, Agent, or Firm* — Nixon & Vanderhye P.C.

(57) ABSTRACT

(Modified) rice endosperm protein is used as novel protective hydrocolloid for active ingredients, especially fat-soluble active ingredients and/or colorants. Included are compositions comprising (modified) rice endosperm protein and at least one active ingredient and to their manufacture, as well as to the (modified) rice endosperm protein itself and its manufacture. These compositions are used for the enrichment, fortification and/or coloration of food, beverages, animal feed, personal care or pharmaceutical compositions, and to food, beverages, animal feed, personal care and pharmaceutical compositions containing such a (modified) rice endosperm protein and such a composition, respectively.

2 Claims, 9 Drawing Sheets

(56) References Cited

OTHER PUBLICATIONS

Ju et al.—"Extraction, denaturation and hydrophobic properties of rice flour proteins," Database Biosis Biosciences Information Service, Philadelphia, PA. , Mar. 2001, XP002424077, Database accession No. PREV200100346268 and Journal of Food Science, vol. 66, No. 2, Mar. 2001, pp. 229-232.

Anderson et al.: "Physicochemical properties of pronase-treated rice glutelin," Database FTSA [online] International Food Information Service (IFIS), Frankfurt-Main, DE, XP002424078, Database accession No. 2001-00-m0938 abstract.

Journal of the American Oil Chemists' Society 78 (1) 1-6 2001 Correspondence (reprint) address, N. Hettiarachchy, Dep. Fayetteville, AR, e-mail, Jun. 1, 2001.

Paraman et al, "Pepsin-Assisted Rice Endosperm Protein Extraction with Improved Functional Properties," IFT Food Chemistry Division Abstract, Report No. 2500764, DSM Nutritional Products Ltd, Switzerland, Aug. 18, 2006, pp. 1-2.

Paraman et al, "Functional Properties of Rice Endosperm Protein Prepared by Enzymatic Hydrolysis and Ultrafiltration," Report No. 2500765, Cereal Chemistry, DSM Nutritional Products Ltd, Switzerland, Feb. 15, 2007, pp. 1-23.

Nat. Biotechnol., Apr. 2005, vol. 23, No. 4, pp. 482-487.

Food Composition and Nutrition Tables 1986/1987, 1986, pp. 498-501.

English translation of Notice of Reasons for Rejection in JP P2008-543745 dated Feb. 28, 2012.

English translation of Office Action in CN200680046283.7 dated Mar. 27, 2012.

Wang et al, "Extraction and Exploitation of Rice Protein", Chinese Academic Journal Electronic Publishing House, Jan. 2004.

Letter from East IP Intellectual Property Services dated May 7, 2012 which includes partial English translation of Wang et al.

Damayanthi E. (20010 Rice Bran Stabilization and y-Oryzanol Content of Two Local Paddy Varieties "IR 64" and Cisadane Muncul, J. Teknol Dan Industri. Pangan, vol. XII, No. 1, pp. 72-76.

Datta et al (2003) Bioengineered 'golden' indicia rice cultivars with beta-carotene metabolism in the endosperm with hygromycin and mannose selection systems, Plant Biotechnol. J. vol. 1, No. 2, pp. 81-90.

Yahoo Answer (2011, updated) Is mannose a reducing sugar? Mypertext document://in.answers.yahoo.com/question/index?qid=20080530131318AAf3cux, p. 1.

Kishimoto et al (2001) Rice α-mannosidase digesting the high mannose glycopepide of glutelin, Physiologia Plantarum, vol. 112, issue 1, pp. 15-24.

Smyth et al (1989) Sugar Content and Activity of Sucrose Metabolism Enzymes in Milled Rice Grain, Plant Physiol. vol. 89, pp. 893-896.

\* cited by examiner

PROTECTIVE, HYDROCOLLOID FOR ACTIVE INGREDIENTS

This application is a divisional of application Ser. No. 12/095,927 filed Nov. 25, 2008 which in turn is the U.S. national phase of International Application No. PCT/EP2006/011873 filed 8 Dec. 2006 which designated the U.S. and claims priority to U.S. Provisional Application No. 60/748,192 filed 8 Dec. 2005, the entire contents of each of which are hereby incorporated by reference.

The present invention is directed to the use of (modified) rice endosperm protein (REP as used herein) as novel protective hydrocolloid for active ingredients, especially fat-soluble active ingredients and/or colorants. Moreover, the present invention is directed to compositions comprising (modified) rice endosperm protein and at least one active ingredient and to their manufacture, as well as to the (modified) rice endosperm protein itself and its manufacture. The present invention is further directed to the use of such compositions for the enrichment, fortification and/or coloration of food, beverages, animal feed, personal care or pharmaceutical compositions, and to food, beverages, animal feed, personal care and pharmaceutical compositions containing such a (modified) rice endosperm protein and such a composition, respectively.

Active ingredients, especially fat-soluble active ingredients or colorants, are often not added as such to food, beverages, animal feed, personal care and pharmaceutical compositions, but in form of formulations of the active ingredient in a hydroprotective colloid for reasons of enhancing properties such as chemical stability, (water-)solubility, free-flowing and controlled release etc. Known hydroprotective colloids are e.g. gelatine of different origin (poultry, bovine, pork, fish) and starch. Since hydroprotective colloids of animal origin are often not desired for religious or allergenic reasons and starch-based hydroprotective colloids might have low preference for consumers who are interested in gluten and corn-free products there is an on-going need for alternative hydroprotective colloids.

Rice endosperm proteins are recognized as nutritional and hypoallergenic and can, thus, be a suitable alternative source of protective hydrocolloid for formulations of active ingredients. However, high insolubility and poor functionality of rice endosperm protein at neutral pH limits its industrial application as a functional ingredient in food and pharmaceuticals products. The present invention overcomes these limitations and incorporates the (modified) rice endosperm protein as a protective hydrocolloid for formulations of active ingredients, especially of fat-soluble active ingredients and/or colorants.

Rice proteins rank high in nutritional quality in comparison to other cereals including corn and wheat, and are therefore perceived to have immense potential uses as food ingredients. Cereal grain proteins are rich in the essential amino acids cysteine and methionine. Lysine is the primary limiting amino acid in cereal proteins, but rice contains more lysine (3.8 g/16 g N) (grams per 16 grams of nitrogen) than other cereal proteins (wheat 2.3, corn 2.5 g/16 g N) (grams per 16 grams of nitrogen) (see reference 4 cited below). Although rice is generally regarded as having the lowest protein content (7.3%) among the common grains (wheat 10.6%, corn 9.8%, barley 11.0%, millet 11.5%), the net protein utilization of rice protein (73.8%) is the highest among the cereal grains (wheat 53.0%, corn 58.0%, barley 62.0%, millet 56.0%).

Compared with other cereal proteins, isolation of rice protein is difficult and therefore costly. The predominant rice protein, glutelin, is hydrophobic and is cross-linked with disulfide bonds. The extracted proteins are highly insoluble in nature and the conditions used in protein isolation further decrease their solubility, and thus have limited application as a functional ingredient. High-protein rice products can be obtained from rice flour by alkali extraction followed by precipitation at the isoelectric pH of the protein. Starch-hydrolyzing enzymes such as alpha-amylase, glucoamylase, and pullulanase are often used to separate proteins in rice flour by solubilizing and removing starch. In addition to starch hydrolyzing enzymes, cellulase and hemicellulase enzymes have been used to further increase the protein content in rice protein concentrate. However, information on suitable extraction methods and functionalities of such isolates is limited. Efficient extraction methods using approved food grade enzymes and chemicals are essential for commercial production and application of rice protein.

This need is fulfilled by the compositions of the present invention which comprise a rice endosperm protein and an active ingredient.

BACKGROUND INFORMATION

1. Fiocchi, A.; Travaini, M.; D'Auria, E.; Banderali, G.; Bernardo, L.; Riva, E. Tolerance to a rice hydrolysate formula in children allergic to cow's milk and soy. Clin Exp Allergy 2003, 33(11), 1576-80.
2. Eggum, B. O.; Cabrera, M. I. Z.; Juliano, B. O. Protein and lysine digestibility and protein quality of cooked Filipino rice diets and milled rice in growing rats. Plant Foods Hum. Nutr. 1992, 43 (2), 163-170
3. Bean, M. M.; Nishita, K. D. Rice flours for baking. In Juliano B. O., editor. Rice chemistry and technology, 2nd ed. St. Paul: Amer Assoc. of Cereal Chemists. 1985, pp 539-556.
4. Juliano, B. O. Rice: chemistry and technology. St. Paul, Minn.: American Association of Cereal Chemists. 1985.
5. Anderson, A.; Hettiarachchy, N. S.; Yu, Z. Y. Physicochemical properties of pronase treated rice glutelin. Journal of the American Oil Chemists' Society 2000, 78 (1), 1-6.
6. Yu, Z. Y.; Hettiarachchy, N. S.; Rath, N. Extraction, denaturation and hydrophobic properties of rice flour proteins. J. Food Sci. 2001, 66 (2), 229-232.
7. Padhye, V. W.; Salunke, D. K. Extraction and characterization of rice proteins. Cereal chem. 1979, 106 (3), 389-393.
8. Tecson, E. M. S.; Esmama, B. V.; Lontok, L. P.; Juliano, B. O. Studies on the extraction and composition of rice endosperm glutelin and prolamin. Cereal Chem. 1971, 168-181.
9. Wen, T. N.; Luthe, D. S. Biochemical characterization of rice glutelin. Plant Physiol. 1985, 78, 172-177.
10. Morita, T.; Kiriyama, S. Mass production method for rice protein isolate and nutritional evaluation. J. Food Sci. 1993, 58 (6), 1939-1406.
11. Griffin, V. K.; Brooks, J. R. Production and size distribution of rice moltodextrin hydrolyzed from milled rice flour using heat stable alpha-amylase. J. Food Sci. 1989, 54, 190-193.
12. Shih, F. F.; Daigle, K. Use of enzymes for the separation of protein from rice flour. Cereal Chem. 1997, 74 (4), 437-441.
13. Shih, F. F.; Champagne, E. T.; Daigle, K.; Zarins, Z. Use of enzymes in the processing of protein products from rice bran and rice flour. Nahrung 1999, 43, 14-18.
14. Shih, F. F.; Daigle, K. W. Preparation and characterization of rice protein isolates. Journal of the American Oil Chemists' Society 2000, 77, 885-889.

15. Tang, S.; Hettiarachchy, N. S.; Eswaranandam, S.; Crandall, P. Protein extraction from heat-stabilized defatted rice bran: II. The role of amylase, celluclast, and viscozyme. J. Food Sci. 2003, 68 (2), 471-470.
16. AACC. Method 46-08. Approved Methods of the American Association of Cereal chemists, 8th ed., vol 2. AACC, St. Paul, Minn. 1990, P 1-2.
17. Laemmli, U. K. Cleavage of structural proteins during the assembly of the head of the bacteriophage T4. Nature 1970, 227, 680-686.
18. Hayakawa, S.; Nakai, S. Relationships of hydrophobicity and net charge to the solubility of milk and soy proteins. J. Food Sci. 1985, 50, 486-491.
19. Bera, M. B.; Mukherjee, R. K. Solubility, emulsifying, and foaming properties of rice bran protein concentrates. J. Food Sci. 1989, 54 (1), 142-145.
20. Pearce, K. N.; Kinsella, J. E. Emulsifying properties of proteins: evaluation of a turbidimetric technique. J. Agric. Food Chem. 1978, 26, 716-722.
21. SAS. 2002. JMP® User's Guide, Version 5. SAS Institute Inc. Cary, N.C.
22. Kolar, C. W.; Richert, S. H.; Decker, C. D.; Steinke, F. H.; Vander, R. J. Isolated soy protein. In New Protein Foods; Altschul, A M., Wilcke, H L., Eds.; Academic Press: New York, 1985; Vol. 5.
23. Biliaderis, C. G. Differential scanning calorimetry in food research: A review. Food Chem. 1983, 10, 239-265.
24. Damodarn, S. Protein-stabilized foams and emulsions. J. Food Sci. 2005, 70 (3), 54-66.

DETAILED DESCRIPTION OF THE INVENTION

Compositions of the Present Invention

Figure 1:
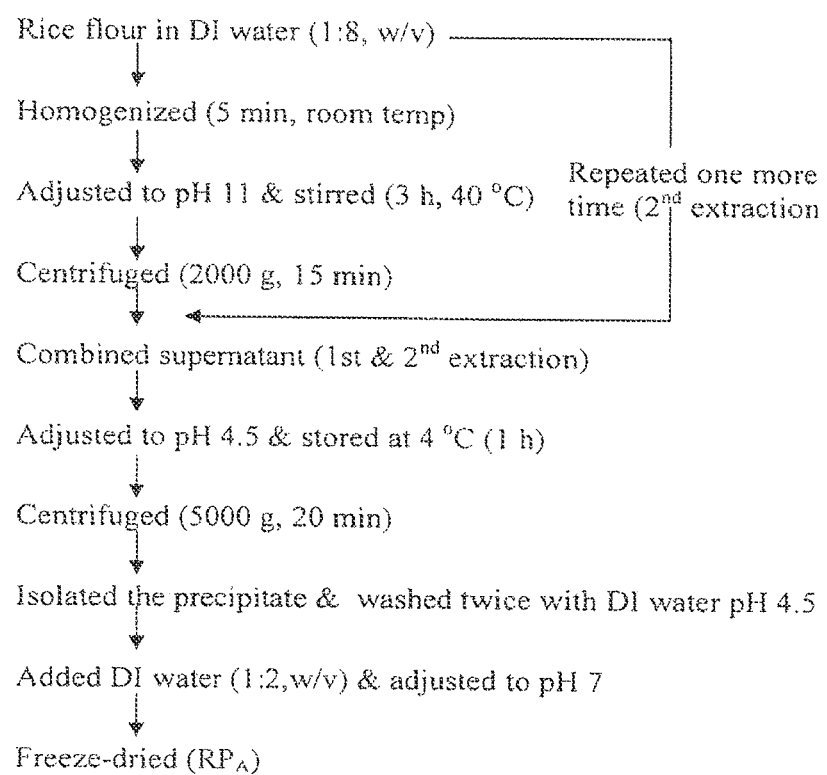
FIG. 1 is a flow chart showing the procedures of methods to prepare rice protein isolates.

The compositions of the present invention may be solid compositions, i.e. stable, water-soluble or water-dispersible powders, or they may be liquid compositions, i.e. aqueous colloidal solutions or oil-in-water dispersions of the aforementioned powders. The stabilised oil-in-water dispersions, which may be oil-in-water emulsions or may feature a mixture of suspended, i.e. solid, particles and emulsified, i.e. liquid, droplets, may be prepared by the methods described below or by an analogous manner.

More specifically, the present invention is concerned with stable compositions in powder form comprising one or more (fat-soluble) active ingredients and/or one or more colorants in a matrix of a (modified) rice endosperm protein.

Preferably the amount of the (modified) rice endosperm protein is from 1 to 70 weight-%, more preferably from 5 to 50 weight-%, even more preferably from 10 to 40 weight-%, most preferably from 10 to 20 weight-% (with 20 weight-% being the most preferred one) and/or the amount of the (fat-soluble) active ingredient and/or colorant is from 0.1 to 90 weight-%, preferably from 1 to 80 weight-%, more preferably from 1 to 20 weight-%, based on the total amount of the composition. If additional adjuvants and/or excipients such as tocopherol and/or ascorbyl palmitate are present, they are present in an amount of from 0.01 to 50 weight-%, preferably in an amount of from 0.1 to 30 weight-%, more preferably in an amount of from 0.5 to 10 weight-%, based on the total amount of the composition.

(Modified) Rice Endosperm Protein

In preferred embodiments of the present invention the rice endosperm protein is a modified rice endosperm protein whose manufacture is described below (see page 13, line 26 till page 18, line 23 and examples 1 to 7). An especially preferred rice protein is one obtained by the following steps: alkaline extraction, (enzymatically modification, especially with ALKALASE® (NOVO NORDISK BIOCHEM, FRANKLINTON, N.C., USA)), centrifugation and ultra-filtration. If needed for the further use the thus obtained modified rice endosperm protein may also be dried.

The invention is, however, not restricted to the use of such manufactured modified rice endosperm proteins.

Even more preferred are (modified) rice endosperm proteins that have an emulsion capacity of $\geq 220$, preferably of $\geq 350$, more preferably of $\geq 500$, even more preferably of from 500 to 1000. Additionally in preferred embodiments of the invention the used (modified) rice endosperm proteins have an emulsion activity of $\geq 0.2$, preferably of $\geq 0.45$, more preferably of $\geq 0.5$, even more preferably of from 0.5 to 1.0. The determination of the emulsion capacity is described in example 8, the determination of the emulsion activity is described in example 9. The present invention refers also to these (modified) rice endosperm proteins themselves.

In further preferred compositions of the present invention the (modified) rice endosperm protein is cross-linked with at least one compound selected from the group consisting of reducing sugars, glycoproteins or glycopeptides.

Active Ingredient

The active ingredients are those ingredients with a pharmacological effect or those providing health benefits to the human or animal body in general. Preferably the active ingredient is a fat-soluble active ingredient and/or a colorant.

The fat-soluble active ingredient and/or the colorant is preferably selected from the group consisting of carotenes and structurally related polyene compounds, fat-soluble vitamins, coenzyme Q10, polyunsaturated fatty acids such as eicosapentaenoic acid (EPA) and docosahexaenoic acid (DHA) and esters thereof (such as the ethyl esters or the triglycerides (containing the same or different fatty acids)), mono-, di-, triglycerides rich in polyunsaturated fatty acids, fat-soluble UV-A filters, UV-B filters, as well as their physiologically acceptable derivatives such as their esters, especially with $C_{1-20}$ carbonic acids, and any mixtures of them.

The most preferred fat-soluble vitamins are Vitamin A or E.

Preferred examples of the carotenes and structurally related polyene compounds are carotenoids such as α-carotene, β-carotene, 8'-apo-β-carotenal, 8'-apo-β-carotenoic acid esters such as the ethyl ester, canthaxanthin, astaxanthin, lycopene, lutein, zeaxanthin, crocetin, α-zeacarotene, β-zeacarotene, as well as their physiologically acceptable derivatives such as their esters, especially with $C_{1-20}$ carbonic acids, and any mixtures of them.

The most preferred carotenoid is β-carotene.

The term "β-carotene" encompasses the all-cis as well as the all-trans isomers and all possible mixed cis-trans-isomers. The same applies for the other carotenoids.

The term "zeaxanthin" encompasses the natural R,R-zeaxanthin, as well as S,S-zeaxanthin, meso-zeaxanthin and any mixture of them. The same applies for lutein.

The (fat-soluble) active ingredients may be of natural origin, i.e. isolated/extracted from plants, purified and/or concentrated, as well as those synthesized by chemical and/or microbiological (fermentative) routes.

Further Components

Beside the active ingredient and the (modified) rice endosperm protein the compositions of the present invention may preferably additionally contain at least one water-soluble antioxidant and/or fat-soluble antioxidant.

The water-soluble antioxidant may be for example ascorbic acid or a salt thereof, preferably sodium ascorbate, water soluble polyphenols such as hydroxytyrosol and oleuropein aglycon; epigallocatechingallate (EGCG) or extracts of rosemary or olives.

The fat-soluble antioxidant may be for example a tocopherol, e.g. dl-α-tocopherol (i.e. synthetic tocopherol), d-α-tocopherol (i.e. natural tocopherol), β- or γ-tocopherol, or a mixture of two or more of these; butylated hydroxytoluene (BHT); butylated hydroxyanisole (BHA); ethoxyquin, propyl gallate; tert. butyl hydroxyquinoline; or 6-ethoxy-1,2-dihydroxy-2,2,4-trimethylquinoline (EMQ), or an ascorbic acid ester of a fatty acid, preferably ascorbyl palmitate or stearate.

The compositions of the present invention may further contain a co-emulgator selected from the group consisting of mono- and diglycerides of fatty acids, polyglycerol esters of fatty acids, lecithins; N-acylated amino acids and derivatives thereof, N-acylated peptides with an alkyl or alkenyl radical, and salts thereof; alkyl or alkenyl ether or ester sulfates, and derivatives and salts thereof; polyoxyethylenated alkyl or alkenyl fatty ethers or esters; polyoxyethylenated alkyl or alkenyl carboxylic acids and salts thereof; N-alkyl or N-alkenyl betaines; alkyltrimethylammonium or alkenyltrimethylammonium and salts thereof; polyol alkyl or alkenyl ether or ester; and mixtures thereof.

Preferred examples of polyol alkyl or alkenyl ethers or esters are sorbitan alkyl or alkenyl esters polyoxyethylenated with at least 20 units of ethylene oxide, such as sorbitan palmitate 20 EO or Polysorbate 40 marketed under the tradename Montanox 40 DF by the company Seppic, sorbitan laurate 20 EO or Polysorbate 20 marketed under the tradename Tween 20 by the company ICI, and sorbitan monostearate.

The formulations according to the present invention may further be pressed into tablets, whereby one or more excipients and/or adjuvants selected from the group consisting of monosaccharides, disaccharides, oligosaccharides and polysaccharides, glycerol, and triglycerides, may be added.

Preferred examples of mono- and disaccharides which may be present in the compositions of the present invention are sucrose, invert sugar, xylose, glucose, fructose, lactose, maltose, saccharose and sugar alcohols.

Preferred examples of the oligo- and polysaccharides are starch, modified starch and starch hydrolysates. Preferred examples of starch hydrolysates are dextrins and maltodextrins, especially those having the range of 5 to 65 dextrose equivalents (DE), and glucose syrup, especially such having the range of 20 to 95 DE. The term "dextrose equivalent" (DE) denotes the degree of hydrolysis and is a measure of the amount of reducing sugar calculated as D-glucose based on dry weight; the scale is based on native starch having a DE close to 0 and glucose having a DE of 100.

The triglyceride is suitably a vegetable oil or fat, preferably corn oil, sunflower oil, soybean oil, safflower oil, rapeseed oil, peanut oil, palm oil, palm kernel oil, cotton seed oil, olive oil or coconut oil.

Solid compositions may in addition contain an anti-caking agent, such as silicic acid or tricalcium phosphate and the like, and up to 10 weight-%, as a rule 2 to 5 weight-%, of water.

Manufacture of the Composition

An object of the present invention is also a process for the manufacture of the composition of the present invention which comprises the following steps:

I) preparing an aqueous solution or colloidal solution of a (modified) rice endosperm protein, II) optionally adding at least a water-soluble excipient and/or adjuvant to the solution prepared in step I), III) preparing a solution or dispersion of at least an active ingredient, preferably of at least a fat-soluble active ingredient and/or colorant, and optionally at least a fat-soluble adjuvant and/or excipient, IV) mixing the solutions prepared in step I) to III) with each other, V) homogenising the thus resulting mixture, VI) optionally adding a cross-linking agent for cross-linking the (modified) rice endosperm protein, VIa) optionally submitting the mixture resulting after having performed step VI) to enzymatic treatment or heat treatment to cross-link the (modified) rice endosperm protein VII) optionally converting the dispersion obtained in step V) and/or VI) into a powder, VIII) optionally drying the powder obtained in step VII), IX) optionally submitting the dry powder to heat treatment or to enzymatic treatment to cross-link the (modified) rice endosperm protein, with the proviso that only step VIa) or step IX) is carried out, but not both, when step VI) is carried out.

Step I

This step is simply performed by adding water to the (modified) rice endosperm protein or vice versa, optionally under stirring. Alternatively homogenization may be possible via ultrasonication.

Preferably the (modified) rice endosperm protein with the preferences as described above is used.

Step II

Water-soluble excipients and/or adjuvants that may be added are e.g. monosaccharides, disaccharides, oligosaccharides and polysaccharides, glycerol and water-soluble antioxidants. Examples of them are given above.

Step III

Active ingredients are those as described above.

The (fat-soluble) active ingredient and/or colorant and optional fat-soluble excipients and adjuvants are either used as such or dissolved or suspended in a triglyceride and/or an (organic) solvent.

Suitable organic solvents are halogenated aliphatic hydrocarbons, aliphatic ethers, aliphatic and cyclic carbonates, aliphatic esters and cyclic esters (lactones), aliphatic and cyclic ketones, aliphatic alcohols and mixtures thereof.

Examples of halogenated aliphatic hydrocarbons are mono- or polyhalogenated linear, branched or cyclic C1- to C15-alkanes. Especially preferred examples are mono- or polychlorinated or -brominated linear, branched or cyclic C1- to C15-alkanes. More preferred are mono- or polychlorinated linear, branched or cyclic C1- to C15-alkanes. Most preferred are methylene chloride and chloroform.

Examples of aliphatic esters and cyclic esters (lactones) are ethyl acetate, isopropyl acetate and n-butyl acetate; and γ-butyrolactone.

Examples of aliphatic and cyclic ketones are acetone, diethyl ketone and isobutyl methyl ketone; and cyclopentanone and isophorone.

Examples of cyclic carbonates are especially ethylene carbonate and propylene carbonate and mixtures thereof.

Examples of aliphatic ethers are dialkyl ethers, where the alkyl moiety has 1 to 4 carbon atoms. One preferred example is dimethyl ether.

Examples of aliphatic alcohols are ethanol, iso-propanol, propanol and butanol.

Furthermore any oil (triglycerides), orange oil, limonen or the like and water can be used as a solvent.

Fat-soluble excipients and/or adjuvants that may be added are e.g. corn oil, mono- or diglycerides of fatty acids, polyglycerol fatty acids, and middle chain triglycerides ("MCT").

Step IV In an alternative process of the present invention step III) is not carried out, but the active ingredient and the optional fat-soluble excipient and/or adjuvant is directly added to the solution of step I) or II).

Step V

For the homogenisation conventional technologies, such as high-pressure homogenisation, high shear emulsification (rotor-stator systems), micronisation, wet milling, microchanel emulsification, membrane emulsification or ultrasonification can be applied. Other techniques used for the preparation of compositions containing (fat-soluble) active ingredients and/or colorant for enrichment fortification and/or coloration of food, beverages, animal feed, cosmetics or pharmaceutical compositions are disclosed in EP-A 0 937 412 (especially paragraphs [0008], [0014], [0015], [0022] to [0028]), EP-A 1 008 380 (especially paragraphs [0005], [0007], [0008], [0012], [0022], [0023] to [0039]) and in U.S. Pat. No. 6,093,348 (especially column 2, line 24 to column 3, line 32; column 3, line 48 to 65; column 4, line 53 to column 6, line 60), the contents of which are incorporated herein by reference.

Step VI

The cross-linking agent is preferably selected from the group consisting of reducing sugars, glycoproteins, and glycopeptides. Thus an intermolecular cross-linking between the (modified) rice endosperm protein and the sugar or sugar part of the glycoprotein/glycopeptide is formed. Preferred examples of the cross-linking agent are the reducing sugars such as glucose, fructose, saccharose and xylose.

Step VIa

The cross-linking can be achieved by submitting mixtures additionally containing a crosslinking agent as described above to heat-treatment to cause cross-linking of the sugar with the protein in a Maillard type reaction, i.e. by thermally treatment, preferably at temperatures from about 30 to about 160° C., more preferably at temperatures form about 70 to about 100° C., most preferably at temperatures from about 80 to about 90° C.

Cross-linking of the (modified) rice endosperm protein with the cross-linking agent can also be achieved by treatment with cross-linking enzymes (acyltransferases, EC 2.3, e.g. transglutaminase, EC 2.3.2.13, protein-glutamine:γ-glutamyltransferase), i.e. by enzymatically treatment, conveniently carried out at temperatures from about 0 to about 70° C., preferably at temperatures from about 20 to about 40° C. Preferably the enzymatic treatment according to step VIa) is a treatment with a cross-linking enzyme, particularly with a transglutaminase.

Enzymatic cross-linking results in stable protein-containing polysaccharide networks, in the case of a transglutaminase by the formation of ε-(γ-glutamyl)-lysine isopeptide bonds. The use of glycoproteins or glycopeptides is preferred for the enzymatic cross-linking.

Both techniques, heat-treatment to cause cross-linking of the sugar with the protein in a Maillard type reaction and enzymatic cross-linking can be used for the incorporation of lipophilic moieties and can be carried out either in a dried form of the composition (step IX), or in an aqueous solution or suspension (step VIa). The enzymatic cross-linking is preferably carried out in an aqueous solution or suspension.

Step VII

The so-obtained dispersion, which is an oil-in-water dispersion, can be converted after removal of the organic solvent (if present) into a solid composition, e.g. a dry powder, using any conventional technology such as spray drying, spray drying in combination with fluidised bed granulation (the latter technique commonly known as fluidised spray drying or FSD), or by a powder-catch technique whereby sprayed emulsion droplets are caught in a bed of an absorbent, such as starch, calcium silicate and silicon dioxide, and subsequently dried.

Spray-drying may be performed at an inlet-temperature of from about 100 to about 250° C., preferably of from about 150° C. to about 200° C., more preferably of from about 160 to about 190° C., and/or at an outlet-temperature (product temperature) of from about 45 to about 160° C., preferably of from about 55 to about 110° C., more preferably of from about 65 to about 95° C.

Step VIII

The drying of the powder obtained in step VII is preferably carried out at a temperature of ≦100° C., preferably at a temperature of from 20 to 100° C., more preferably at a temperature of from 60 to 70° C. If the drying is performed in vacuum the temperature is lower.

Step IX

The cross-linking via heat-treatment is carried out as already described above for step VIa. The same applies for the enzymatic treatment, which is, however, preferably carried out in solution/suspension.

Manufacture of the (Modified) Rice Endosperm Protein

The present invention is also directed to a process for the manufacture of a (modified) rice endosperm protein starting from milled rice, whereby the rice bran was removed before milling, comprising the following steps a) to e) with the proviso that at least one of the steps b), c) and d) is carried out:

a) preparing an aqueous solution or suspension of milled rice, whereby the rice bran was removed before milling, whereby the solution or suspension preferably has a dry mass content of from 0.1 to 30 weight-%, preferably from 10 to 15 weight-%, based on the total amount of the aqueous solution or suspension;
b) optionally removing the non-protein part or the protein part of the milled rice, whereby the rice bran was removed before milling, to obtain the rice endosperm protein;
c) optionally modifying the protein part of the milled rice, whereby the rice bran was removed before milling, to obtain modified rice endosperm protein;
d) optionally isolating the (modified) rice endosperm protein;
e) optionally converting the (modified) rice endosperm protein into a solid form.

In the context of the present invention "rice endosperm protein" means especially the product obtained by performing either steps a) and b); or steps a) and d); or steps a), b) and e); or steps a), b) and d); or steps a), d) and e); or steps a), b), d) and e). Preferred are the embodiments where steps a) and b) (and d) and/or e)) are performed, especially preferred are the embodiments where steps a), b) and d) (and e)) are performed.

In the context of the present invention "modified rice endosperm protein" means especially the product where step c) is carried out, i.e. the product obtained by performing either steps a) and c); or steps a), b) and c); or steps a), c) and d); or steps a), c) and e); or steps a), b) c) and d); or steps a), c), d) and e); or steps a), b), c) and e); or steps a), b), c), d) and e).

The modified rice endosperm protein (and its preferences) are more preferred than the rice endosperm protein. Most preferred is the product obtained by performing steps a), b), c) and d) (and e)).

Step a)

Milled rice, where the rice bran was removed before milling, is also known under the expression "rice flour".

This step is simply performed by adding water to the rice flour or vice versa, optionally by stirring vigorously (with a mechanical stirrer) until the rice flour is completely dispersed, or by homogenizing the rice flour suspension with a homogenizer, e.g. for 5 minutes at room temperature.

Step b)

Removing of the Non Protein Part

Step b) may preferably be achieved by treating the rice flour with non-protein degrading enzymes, e.g. with a 0.5% aqueous suspension of TERMAMYL® at a temperature of 90° C. for 2 hours and then with a 0.1% aqueous suspension of a cellulase at a temperature of 50° C. for 30 minutes—without any pH adjustment (pH 6-7), deactivating the enzymes, separating and removing the non-protein part from the protein part of the rice flour.

Preferred examples of non-protein degrading enzymes are starch-degrading enzymes such as α-amylases and cellulases, i.e. cellulose-degrading enzymes, and mixtures thereof. A preferred example of an α-amylase is TERMAMYL 120, Type L, commercially available from Novo Nordisk Biochem, North America, Inc., USA. Other preferred examples are LIQUZYME® Supra, commercially available from Novo Nordisk Biochem, North America, Inc., USA, Amylase S "Amano" 35 G, commercially available from Amano Pharmaceutical Co. Ltd., Nagoya, Japan, Multifect Cellulase, commercially available from Genencor International, Inc., USA, and Cellulase T "Amano" 4, commercially available from Amano Pharmaceutical Co. Ltd., Nagoya, Japan.

The reaction of the enzymes can be stopped by neutralising the solution or suspension if an inorganic acid (e.g. hydrochloric acid) or an organic acid (e.g. citric acid) or base is used or by heating to denature the enzymes.

The denaturation may be achieved by heating the solution to a temperature of from 80 to 95° C., preferably to a temperature of from 80 to 85° C. (especially at a low pH of from 3.5 to 4.5) for 10 to 15 minutes. Afterwards the solution may be cooled to 50° C.

The separation of the non-protein part may be achieved by centrifugation (5000 g for 15 minutes) (whereby the non-protein part is in the water phase), followed by washing with deionized water. The rice endosperm protein remains in pellets.

Removing of the Protein Part

Alternatively a so-called "alkaline extraction" or a so-called "salt-extraction" may be performed before the centrifugation or filtration.

"Alkaline extraction" means that first the pH of the solution or suspension of the rice flour is adjusted to a value of from 7 to 12, preferably to a value of from 8 to 10, more preferably to a value of about 9, with an alkali solution (e.g. an aqueous NaOH solution) at 40 to 60° C. for 3 hours.

In cases where the protein yield is more important than the protein functionality it may be advantageous to adjust the pH preferably to a value of from 8 to 12, more preferably of from 9 to 12, even more preferably from 10 to 12.

Preferably such a base has a concentration of about 0.1 to 5 M, preferably of about 0.5 to about 2 M. The base may be an inorganic base. Examples of inorganic bases are (earth) alkali hydroxides such as sodium hydroxide (preferred), potassium hydroxide and calcium hydroxide.

A "salt-extraction" is similar to an "alkali-extraction", but in addition to the base a salt such as sodium chloride is used. In a preferred embodiment of the invention an aqueous 0.08 M sodium chloride solution (adjusted to pH 11 with NaOH) is used as the extracting solvent.

In both cases (alkaline or salt extraction) the protein part is transferred to the water phase. The protein part may be separated then by centrifugation or filtration from the non-protein part.

Step c)

The modification of the rice flour may be achieved by treating it(s protein part) with (commercially available) food grade alkaline, neutral and/or acid proteases. For some proteases the enzyme specifications and the optimum conditions are given in the examples.

The proteases may be from bacteria or fungi, as well as from fruit or may have animal origin.

Examples of alkaline proteases are the commercially available ALKALASE® (Novo Nordisk Biochem, Franklinton, N.C., USA), ALKALINE PROTEASE® (Enzyme Development Corporation, New York, N.Y., USA), PROTEX 6L® (GENENCOR® Bacterial Alkaline Protease, Genencor International, Inc., Rochester, N.Y., USA) and GENENCOR® Protease 899 (Genencor International, Inc., Rochester, N.Y., USA).

Examples of neutral proteases are the commercially available BROMELAIN® (Enzyme Development Corporation, New York, N.Y., USA), LIQUIPANOL® (Enzyme Development Corporation, New York, N.Y., USA) and bacterial neutral-protease (Genencor International, Inc., Rochester, N.Y., USA). A further example of a neutral protease is the commercially available COLLUPILIN® of DSM Food Beverages, Delft, Netherlands, produced from *Carica papaya*, a plant, i.e. an enzyme of fruit origin.

Examples of acid proteases are pepsin (Sigma, USA) and Acid protease (Amano Pharmaceutical Co. Ltd., Nagoya, Japan).

In a preferred embodiment of the process of the present invention the protein part of the rice flour is treated subsequently by two different alkaline proteases at a pH range of from 7 to 10 for 10 to 80 minutes at 40 to 60° C.

Preferably one of these proteases is a serine specific protease such as ALKALASE® (NOVO NORDISK BIOCHEM, FRANKLINTON, N.C., USA), PROTEX 6L or ALKALINE PROTEASE and the other is a cysteine specific protease such as LIQUIPANOL® (ENZYME DEVELOPMENT CORPORATION, NEW YORK, N.Y., USA) or BROMELAIN.

The step may also be modified by not adding the enzyme(s) at once but by adding them (subsequently or simultaneously) portion wise.

Step c) may also be performed after step d), i.e. first the rice endosperm protein is isolated and then it is modified.

Step d)

Step d) is preferably carried out by centrifugation and/or filtration, preferably by ultrafiltration. The ultrafiltration may be carried out without prior centrifugation.

After enzyme inactivation, the hydrolyate may be preferably centrifuged at low speed (1000 g for 10 minutes) to separate insoluble proteins and impurities.

The soluble fractions of the protein hydrolysates may then be filtered through Whatman #0.4 filter paper and the filtrate be subjected to a sequential ultrafiltration (UF) and diafiltration (DF) with membranes with a molecular weight cut-off (MWCO) of ≥5 kDa, preferably with membranes with a molecular weight cut-off (MWCO) of ≥30 kDa, more preferably with membranes with a molecular weight cut-off (MWCO) of ≥50 kDa, most preferably with membranes with a molecular weight cut-off (MWCO) of from 50 to 750 kDa.

Ultrafiltration and diafiltration may be performed at room temperature with an inlet pressure of from 20 to 25 psi and an outlet-pressure of 10 psi. The solution may then be ultrafiltrated to a concentration factor of 5 Immediately after ultrafiltration, the retenate may be diafiltrated two times with twice the volume of deionized water. During ultrafiltration and diafiltration the pH of the solution may be maintained between pH 8.0 and 9.0 in order to keep the protein soluble.

Step e)

The conversion into a solid form, e.g. a dry powder, can be achieved by any drying method known to the person skilled in the art. Preferred are spray drying or freeze-drying. Spray drying is preferably performed at an inlet temperature of about 200° C. to about 210° C. and at an outlet temperature of about 70° C. to about 75° C. The freeze-drying is preferably performed at a temperature of from about −20° C. to about −50° C. for 10 to 48 hours.

An object of the present invention is also the (modified) rice endosperm protein obtainable by any process as described above.

INDUSTRIAL APPLICABILITY

The present invention is directed to the use of a composition as described above for the enrichment, fortification and/or coloration of food, beverages, animal feed, personal care or pharmaceutical compositions, as well as to the food, beverages, animal feed, personal care and pharmaceutical compositions containing such a composition as described above themselves.

The present invention is also directed to food, beverages, animal feed, personal care and pharmaceutical compositions containing a (modified) rice endosperm protein as described above, as well as to the use of such a (modified) rice endosperm protein, preferably such as described above, as protective hydrocolloid for active ingredients, especially fat-soluble active ingredients and/or colorants.

Animals including humans in the context of the present invention encompass besides humans especially farm animals such as sheep, cow, horses, poultry (broiler and egg pigmentation), shrimps and fish (especially salmon and rainbow trout) as well as pets such as cat, dogs, birds (e.g. flamingos) and fish.

Beverages wherein the compositions of the present invention can be used, especially as a colorant or a functional ingredient, can be carbonated beverages e.g., flavoured seltzer waters, soft drinks or mineral drinks, as well as non-carbonated beverages e.g. flavoured waters, fruit juices, fruit punches and concentrated forms of these beverages. They may be based on natural fruit or vegetable juices or on artificial flavours. Also included are alcoholic beverages and instant beverage powders. Besides, sugar containing beverages, diet beverages with non-caloric and artificial sweeteners are also included.

Further, dairy products, obtained from natural sources or synthetic, are within the scope of the food products wherein the compositions of the present invention can be used, especially as a colorant or as a functional ingredient. Typical examples of such products are milk drinks, ice cream, cheese, yoghurt and the like. Milk replacing products such as soymilk drinks and tofu products are also comprised within this range of application.

Also included are sweets which contain the compositions of the present invention as a colorant or as a functional ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the compositions of the present invention as a colorant or a functional ingredient. Furthermore, fruit preparations used for dairy and cereals are also included.

The final concentration of the (fat-soluble) active ingredient and/or the colorant which is added via the compositions of the present invention to the food products may be from 0.1 to 500 ppm, particularly from 1 to 50 ppm, based on the total weight of the food composition and depending on the particular food product to be coloured or fortified and the intended grade of coloration or fortification.

The food compositions of this invention are preferably obtained by adding to a food product the (fat-soluble) active ingredient and/or the colorant in the form of a composition of this invention. For coloration or fortification of a food or a pharmaceutical product a composition of this invention can be used according to methods per se known for the application of water dispersible solid compositions of the present invention.

In general the composition may be added either as an aqueous stock solution, a dry powder mix or a pre-blend with other suitable food ingredients according to the specific application. Mixing can be done e.g. using a dry powder blender, a low shear mixer, a high-pressure homogeniser or a high shear mixer depending on the formulation of the final application. As will be readily apparent such technicalities are within the skill of the expert.

Pharmaceutical compositions such as tablets or capsules wherein the compositions are used as a colorant are also within the scope of the present invention. The coloration of tablets can be accomplished by adding the compositions of the present invention in form of a liquid or solid colorant composition separately to the tablet coating mixture or by adding a colorant composition to one of the components of the tablet coating mixture. Coloured hard or soft-shell capsules can be prepared by incorporating a colorant composition in the aqueous solution of the capsule mass.

Pharmaceutical compositions such as tablets such as chewable tablets, effervescent tablets or filmcoated tablets or capsules such as hard shell capsules wherein the compositions are used as an active ingredient are also within the scope of the present invention. The compositions of the present invention are typically added as powders to the tableting mixture or filled into the capsules in a manner per se known for the production of capsules.

Animal feed products such as premixes of nutritional ingredients, compound feeds, milk replacers, liquid diets or feed preparations wherein the compositions are either used as a colorant for pigmentation e.g. for egg yolks, table poultry, broilers or aquatic animals (especially shrimps, salmon, rainbow trout) or as an active ingredient are also within the scope of the present invention.

Personal care compositions: Cosmetics, toiletries and derma products i.e. skin and hair care products such as creams, lotions, baths, lipsticks, shampoos, conditioners, sprays or gels wherein the compositions are used as a colorant or as an active ingredient are also within the scope of the present invention.

The present invention is further illustrated by the following examples.

EXAMPLES

The following abbreviations are used:
UF=ultrafiltration
DF=diafiltration
DH=degree of hydrolysis
DI water=deionized water
MWCO=molecular weight cut off
SDS=sodium dodecyl sulfate Rice flour was obtained from Riceland Foods (Stuttgart, Ark.). The following food grade enzymes were used in isolating protein. (1) TERMAMYL—Heat stable alpha-amylase, Novo Nordisk Biochem, North America, Inc, USA, (3) Multifect Cellulase—Fungal Cellulase, 2,000 IU/g, Genencor International, Inc., USA. Food grade proteases with the following specifications were used (Table 1a & 1b).

TABLE 1a

Enzyme specification I

| Enzyme | Type of protease | Source | Preferential specificity |
| --- | --- | --- | --- |
| Protex 6L | Serine Protease | Bacillus licheniformis | Hydrolysis of proteins with broad specificity for peptide bonds |
| Bromelain | Cysteine Protease | Pineapple stem | Broad specificity, but strong preference for Arg-Arg in peptides |
| ALKALASE ® (Novo Nordisk Biochem, Franklinton, NC, USA) | Serine Protease | Bacillus licheniformis | Broad specificity, and a preference for a large uncharged residue's carboxyl sites |
| LIQUIPANOL ® (Enzyme Development Corporation, New York, NY, USA) | Cysteine Protease | Concentrated papain | Broad specificity |
| Alkaline protease | Serine Protease | Bacterial protease | Hydrolysis of proteins with broad specificity for peptide bonds |
| Pepsin | Aspartic Protease | Porcine stomach | The C-terminal side of tyrosine, phenylalanine, and tryptophan residues |

TABLE 1b

Enzyme specification II

| Enzymes | pH-range | Activity/g | Company |
| --- | --- | --- | --- |
| Protex 6L | 6-10 | 580 000 | Genencor International, Inc., Rochester, NY 14618, USA |
| Bromelain | 5-8 | 150 000 | Enzyme Development Corporation, New York, NY 10001, USA. |
| ALKALASE ® (Novo Nordisk Biochem, Franklinton, NC, USA) | 6-9 | 2.4 AU | Novo Nordisk Biochem, Franklinton, NC 27525, USA |
| LIQUIPANOL ® (Enzyme Development Corporation, New York, NY, USA) | 5-8 | 125 000 | Enzyme Development Corporation, New York, NY 10001, USA. |
| Alkaline protease | 6-9 | 175 000 | Enzyme Development Corporation, New York, NY 10001, USA. |

SUMMARY

Experiments were conducted with optimization of isolating rice endosperm proteins by alkali, salt, and enzymatic methods and evaluating them for their extractability and physicochemical and functional properties. The objectives were to optimize the extraction process, and evaluate the physicochemical properties of the extracts in order to identify the optimum extraction methods for improved rice protein functionality.

Rice protein isolates were prepared by chemical and enzymatic methods. Preliminary trials were conducted to optimize the extraction conditions of protein with maximum yield and protein content. Examples of the procedures of chemical and enzymatic methods are given in FIG. 1 of rice protein isolate preparation RPA and for rice protein isolate preparation ($RP_{ET}$) by TERMAMYL treatment at 90° C. followed by cellulase treatment in FIG. 2.

Isolation of the (Modified) Rice Endosperm Protein by Filtration

The ultrafiltration experiments were carried out with a Romicon ultrafiltration system (Koch membrane systems, USA) equipped with 1" diameter Hollow-fiber Polysulfone membrane cartridges. The soluble fractions of (modified) rice endosperm protein were filtered through Whatman #0.4 filter paper and the filtrate was subjected to a sequential ultrafiltration with membrane-cartridges having nominal molecular weight cut off (MWCO) of 50, 30, 10, and 5 kDa. In each MWCO cartridges, the solution was ultrafiltrated at a concentration factor of 5 Immediately after ultrafiltration, the retenate was diafiltrated two times with twice the volume of deionized water. The permeates of the first (50 kDa) ultrafiltration (UF) and diafiltrations (DF) were pooled and subjected to next MWCO (30 kDa) UF & DF. The resulted retenates from each of the MWCO cartridges were freeze-dried and evaluated for DH, solubility & emulsifying properties.

(A) Protein Extraction

Example 1

Isolation of the Rice Endosperm Protein by Alkaline Extraction ("Chemical Extraction")

Example 1-1

REP 1-1

Five hundred grams of rice flour were homogenized with 4 L deionized water (1:8, w/v) in a blender for 5 minutes at setting 6 (Virtishear Tempest, The Virtis Co., Gardiner, N.Y., U.S.A.) at room temperature. The slurry was adjusted to pH 11.0 using 1 N NaOH, and the suspension was stirred for 3 hours at 40° C. The solubilized protein in the solution was separated by centrifugation (5,000 g, 20 minutes). This procedure was repeated once again to extract more from the residue. Proteins in combined supernatants of first and second extractions were isoelectrically precipitated at pH 4.5 and kept for 2 hours at 4° C. The precipitate was recovered by centrifugation at 10,000 g for 20 minutes, washed twice with deionized water (1:4, w/v, pH 4.5), adjusted to pH 7.0, freeze dried, and stored at 5° C.

Alternative Example 1-2

REP 1-2

5 Kg rice flour was homogenized with 40 L of deionized water (1:8, w/v), and the pH of the slurry was adjusted to pH 11 by adding 3 N NaOH, and the suspension was stirred for 3 hours at 40° C. The solubilized protein in the solution was separated by centrifugation (5000 g, 15 min) This procedure was repeated one more time to extract more from the residue. Proteins in the combined supernatants of first and second extractions were isoelectrically precipitated at pH 4.5 and kept for 2 hours at 4° C. The precipitate was recovered by centrifugation at 5000 g for 20 min, washed twice with deionized water (1:4, w/v, pH 4.5), adjusted to pH 7.0, and stored at 5° C.

Alternative Example 1-3

REP 1-3

One kilogram of rice flour was homogenized with 8 L deionized water (1:8, w/v) in a homogenizer (Virtishear Tempest, The Virtis Co., Gardiner, N.Y., U.S.A.) for 5 min. The pH of the slurry was adjusted to 11 using 1 N NaOH and the suspension was stirred for 3 h at 40° C. The solubilized protein in the solution was separated by centrifugation (2000 g, 15 min). This procedure was repeated to extract additional protein from the residue. Proteins in combined supernatants of first and second extractions were isoelectrically precipitated at pH 4.5 and kept at 4° C. for 1 h. The precipitate was recovered by centrifugation at 5000 g for 20 min, washed with deionized water (1:4, w/v, pH 4.5), adjusted to pH 7.0, freeze dried (RPA), and stored at 5° C. (FIG. 1).

Example 1-4

(REP 1-4): Isolation of the rice endosperm protein by salt extraction

Salt extraction of rice protein ($RP_S$) was similar to the above alkali method (see REP 1-3) but a combined solution of 0.08 M sodium chloride (adjusted to pH 11 with NaOH) was used as the extracting solvent.

Example 2

Isolation of the Rice Endosperm Protein by Enzymatic Degradation of the Non-Protein Part ("Enzymatic Extraction")

Example 2-1

REP 2-1

Five hundred grams of rice flour were dispersed in 3 L distilled water (1:6, w/v). The rice flour-water was stirred for 15 minutes at 40° C. to form a slurry. The slurry was treated with 0.5% alpha-amylase and the temperature was gradually raised to 90° C. and incubated for 2 hours at 90° C. Solubilized starch was removed by centrifugation at 5,000×g for 15 minutes at 20° C. The residue was again mixed with 1.5 L deionized water and treated with 0.1% cellulase and incubated at 50° C. for 30 minutes. The enzymes were inactivated by lowering the pH to 3.5 at 90° C. Solubilized starch and cellulose fractions were removed by centrifugation at 5000×g for 15 minutes. The precipitated protein was washed twice with warm deionized water to remove soluble sugar and remaining enzyme, adjusted to pH 7.0, freeze-dried, and stored at 5° C.

Alternative Example 2-2

REP 2-2

5 Kg of rice flour was homogenized with 30 L deionized water and stirred for 15 min at 60° C. The slurry was treated with 0.2% TERMAMYL, and the temperature was gradually raised to 90° C. and incubated at that temperature for 2 hours. The solubilized starch was removed by filtering with cheese cloth. The pellet was again mixed with 15 L deionized water, and incubated with 0.1% pectinase at 50° C. for 30 min, and added another 0.1% enzyme TERMAMYL. The temperature was gradually raised to 90° C. and incubated at that temperature for 30 min. The enzymes were inactivated by lowering the pH to 5.0 at 90° C. The solubilized cell wall components and residual starch were removed by filtering with cheese cloth. The protein pellet was washed twice with warm deionized water to remove remaining soluble sugars and enzymes, adjusted to pH 7.0, stored at 5° C.

Alternative Example 2-3

REP 2-3

Figure 2:
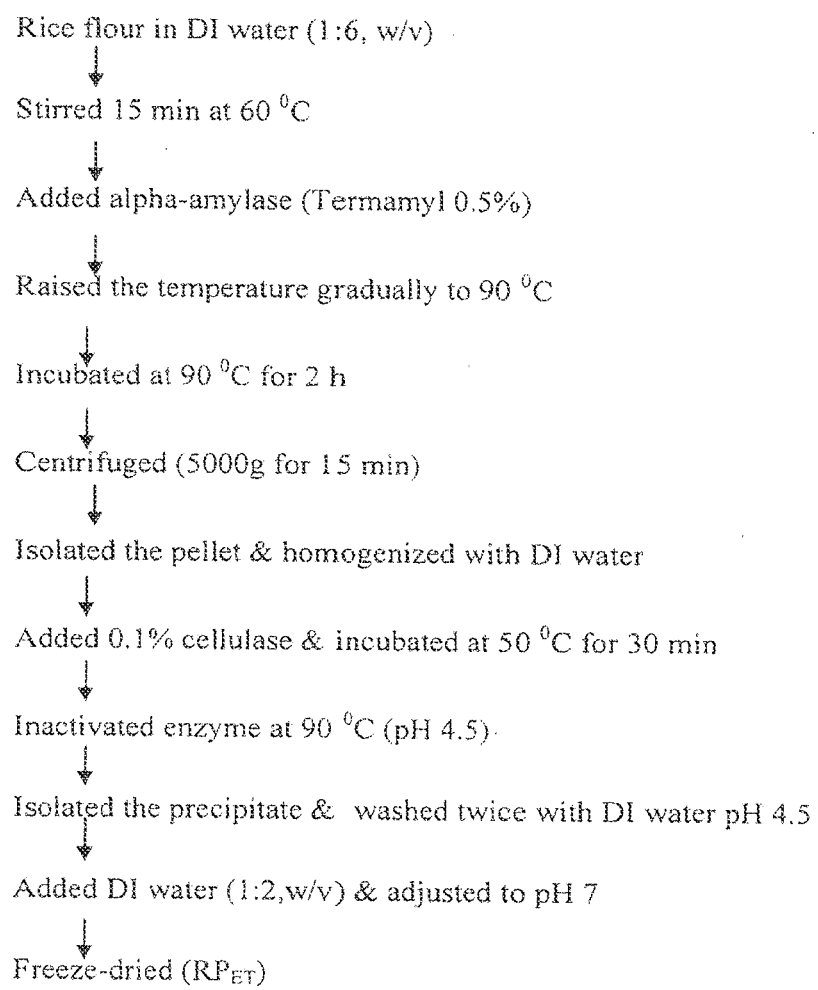
FIG. 2 is a flow chart showing cellulase treatment following the treatment shown in FIG. 1.

One kilogram of rice flour was homogenized with 6 L deionized water and stirred for 15 min at 60° C. The slurry was treated with 0.5% TERMAMYL, and the temperature was gradually raised to 90° C. and incubated at that temperature for 2 h. The solubilized starch was removed by centrifugation (5000 g, 15 min) The pellet was again mixed with 3 L deionized water and incubated with 0.1% cellulase at 50° C. for 30 min. The enzymes were inactivated by lowering the pH to 4.5 at 90° C. Then a solubilized cellulose fraction was removed by centrifugation. The precipitated protein was washed twice with warm deionized water to remove soluble sugar and remaining enzyme, adjusted to pH 7.0, freeze-dried ($RP_{ET}$), and stored at 5° C. (FIG. 2).

Alternative Example 2-4

REP 2-4

The amylase S ($RP_{EA}$) extraction was essentially the same as the TERMAMYL method (see REP 2-3) except that amylase S was used instead of TERMAMYL. The amylase S has an optimum activity at 70° C., providing a milder extraction condition than the TERMAMYL method working at 90° C. The moisture, protein, starch, fiber, fat, and ash contents of the protein isolates were determined as disclosed in Approved Methods of the American Association of Cereal Chemists, 8th Ed., Vol. 2, AACC, St. Paul, Minn., 1990, p 1-2; Method 46-08.

(B) Protein modification

Example 3

Modification of Alkali-Extracted Rice Endosperm Protein by Protease

REP 3-1 to 3-8

Detailed Description for Preparation of REP 3-1 to REP 3-5

Alkali extracted rice endosperm protein isolate REP 1-1 was subjected to protease treatment. The protein was mixed with deionized water (1:12.5, w/v), homogenized, adjusted to the optimum pH of each enzyme, and stirred at 50° C. for 10 minutes. The dispersion was treated with food grade proteases under optimized conditions of each enzyme. The optimized conditions for each enzyme are given in Table 2. Proteases of commercial food grade (BROMELAIN (REP 3-1), PROTEX 6 L (REP 3-2), pepsin (REP 3-3), ALKALASE® (NOVO NORDISK BIOCHEM, FRANKLINTON, N.C., USA) (REP 3-4), and LIQUIPANOL® (ENZYME DEVELOPMENT CORPORATION, NEW YORK, N.Y., USA) (REP 3-5)), were used to improve the solubility and functional properties. The degree of hydrolysis of the resulting hydrolysates has been optimized by OPA method (Nielsen et al, Journal of Food Science 2001, 66(5), 642-646) to maximize the functional properties. The enzymatic-reactions were terminated at required DH by the specific inactivation conditions of each enzyme. The hydrolyzed products were spray dried and stored at 5° C.

TABLE 2

The optimum enzyme conditions used in protein hydrolysis

| Enzyme | Amount of Enzyme [weight-%, based on protein weight] | pH | Temperature [° C.] | Time [minutes] |
|---|---|---|---|---|
| LIQUIPANOL ® (Enzyme Development Corporation, New York, NY, USA) | 1.0 | 8.0 | 50 | 60 |
| Bromelain | 1.0 | 7.0 | 50 | 60 |
| ALKALASE ® (Novo Nordisk Biochem, Franklinton, NC, USA) | 1.0 | 9.0 | 60 | 60 |
| Protex 6L | 1.0 | 10.0 | 60 | 60 |
| Pepsin | 0.5 | 3.0 | 37 | 30 |

Figure 4:
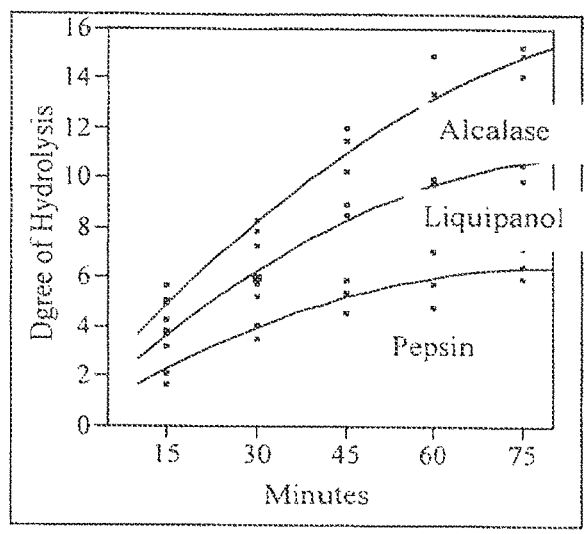
FIG. 4 shows the hydrolysis profiles of the rice endosperm protein treatment with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or pepsin as a function of hydrolysis time.

FIG. 4 shows the hydrolysis profiles of the rice endosperm protein treated with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or Pepsin as a function of the hydrolysis time.

Figure 7:
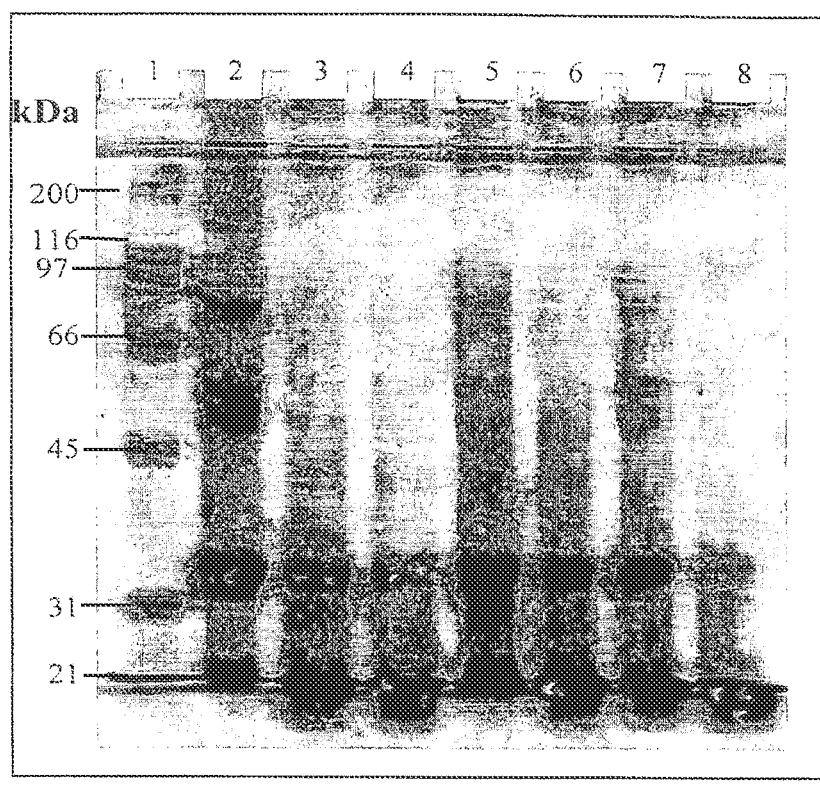
FIG. 7 shows the molecular size profiles of rice proteins and hydrolysate produced by treatment with pepsin, LIQUIPANOL® (ENZYME DEVELOPMENT CORPORATION, NEW YORK, N.Y., USA) and ALKALASE® (NOVO NORDISK BIOCHEM, FRANKLINTON, N.C., USA) as determined by SDS PAGE gel electrophoresis.

FIG. 7 shows the molecular size profiles of rice proteins and hydrolysate produced by treatment with pepsin, LIQUIPANOL® (Enzyme Development Corporation, New York, N.Y., USA), and ALKALASE® (NOVO NORDISK BIOCHEM, FRANKLINTON, N.C., USA) determined by SDS PAGE gel electrophoresis:
Lane 1—Standard marker;
Lane 2—Rice protein (control);
Lane 3—Pepsin 2.2% DH;
Lane 4—Pepsin 6.5% DH;
Lane 5—LIQUIPANOL® (Enzyme Development Corporation, New York, N.Y., USA) 3.9% DH;
Lane 6—LIQUIPANOL® (Enzyme Development Corporation, New York, N.Y., USA) 10.5% DH;
Lane 7—ALKALASE® (Novo Nordisk Biochem, Franklinton, N.C., USA) 7.7% DH;
Lane 8—ALKALASE® (Novo Nordisk Biochem, Franklinton, N.C., USA) 14.7% DH.

Figure 8:
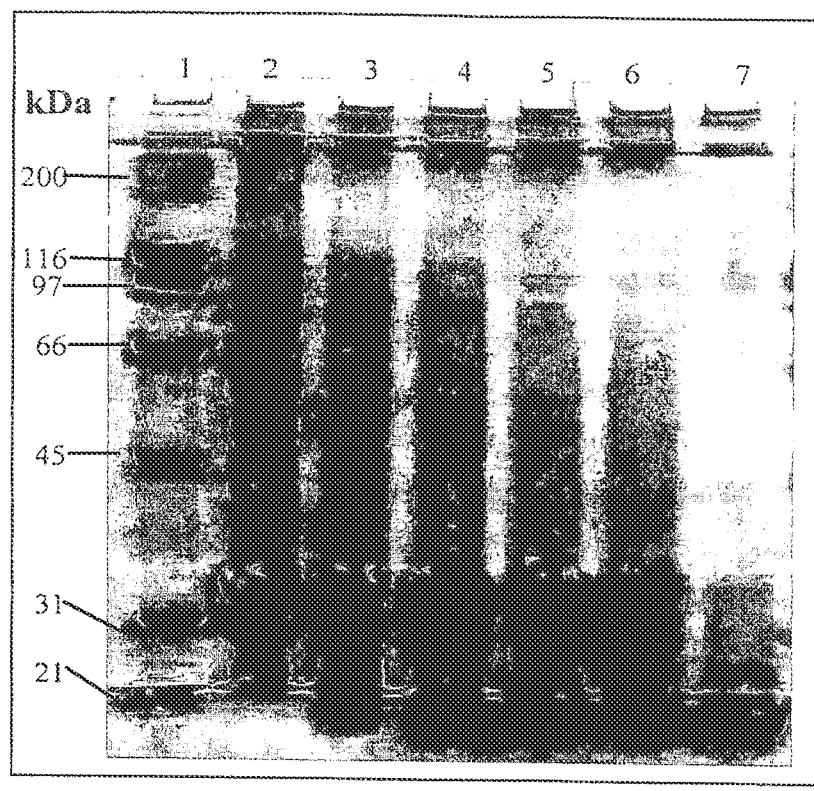
FIG. 8 shows the molecular size profiles of rice protein hydrolysate determined by SDS PAGE gel electrophoresis.

FIG. 8 shows the molecular size profiles of ALKALASE® (NOVO NORDISK BIOCHEM, FRANKLINTON, N.C., USA) treated rice protein hydrolysate determined by SDS PAGE gel electrophoresis:
Lane 1—Standard marker;
Lane 2—Rice protein (control);
Lane 3—ALKALASE® (Novo Nordisk Biochem, Franklinton, N.C., USA) 5.2% DH;
Lane 4—ALKALASE® (Novo Nordisk Biochem, Franklinton, N.C., USA) 7.7%;
Lane 5—ALKALASE® (Novo Nordisk Biochem, Franklinton, N.C., USA) 11.2%;
Lane 6—ALKALASE® (Novo Nordisk Biochem, Franklinton, N.C., USA) 13.5%;
Lane 7—ALKALASE® (Novo Nordisk Biochem, Franklinton, N.C., USA) 14.7% DH.

Detailed Description for Preparation of REP 3-6, 3-7, and 3-8

REP 1-2 was used for the preparation of REP 3-6, REP 3-7 and REP 3-8 instead of REP 1-1 as in examples REP 3-1, REP 3-2, REP 3-3, REP 3-4 and REP 3-5.

REP 3-6

Alkali extracted rice protein isolate REP 1-2 was homogenized with DI water (8% w/v) and, adjusted to pH 8.0. The protein solution was treated with 1% ALKALASE® (NOVO NORDISK BIOCHEM, FRANKLINTON, N.C., USA) at 50° C. for 3.5 min. The enzyme was inactivated at 70° C. at pH 5.0 for 15 minutes. The protein hydrolysate (REP 3-6) was spray dried and stored at 5° C.

REP 3-7

Alkali extracted rice protein isolate REP 1-2 was homogenized with DI water (8% w/v) and, adjusted to pH 8.0. The protein solution was treated with 1% ALKALASE® (NOVO NORDISK BIOCHEM, FRANKLINTON, N.C., USA) at 50° C. for 7.5 min. The enzyme was inactivated at 70° C. at pH 5.0 for 15 minutes. The protein hydrolysate (REP 3-7) was spray dried and stored at 5° C.

REP 3-8

Alkali extracted rice protein isolate REP 1-2 was homogenized with DI water (8% w/v) and, adjusted to pH 8.0. The protein solution was treated with 1% ALKALASE® (NOVO NORDISK BIOCHEM, FRANKLINTON, N.C., USA) at 50° C. for 11 minutes. The enzyme was inactivated at 70° C. at pH 6.0 for 15 minutes. The protein hydrolysate (REP 3-8) was spray dried and stored at 5° C.

Example 4

Modification of alkali-extracted rice endosperm protein by two type proteases (REP 4)

Alkali extracted rice endosperm protein isolate (REP 1) was subjected to a combined treatment with serine and cysteine protease. The protein was mixed with deionized water (1:12.5, w/v), homogenized, adjusted to pH 9.0 and stirred at 60° C. for 10 minutes. The dispersion was treated with food grade ALKALASE® (NOVO NORDISK BIOCHEM, FRANKLINTON, N.C., USA) 2.4 L (0.5%) and incubated at 60° C. for 15 minutes. Then the LIQUIPANOL® (ENZYME DEVELOPMENT CORPORATION, NEW YORK, N.Y., USA) (0.5%) was added to the reaction mixture and incubated at 50° C. for 15 minutes. The enzymatic-reactions were terminated at 80° C. for 10 minutes and the modified rice endosperm protein was spray dried and stored at 5° C.

Example 5

Modification of Alkali-Extracted Rice Endosperm Protein by Protease and Subsequent Ultra- and Diafiltration of Said Modified Rice Endosperm Protein (REP 5)

Alkali extracted rice endosperm protein isolate (REP 1) was subjected to extended hydrolysis by a combined treatment with serine and cysteine protease: The protein was mixed with deionized water (1:12.5, w/v), homogenized, adjusted to pH 9.0 and stirred at 60° C. for 10 minutes. The dispersion was treated with food grade ALKALASE® (NOVO NORDISK BIOCHEM, FRANKLINTON, N.C., USA) 2.4 L (0.5%) and incubated at 60° C. for 60 minutes. Then the LIQUIPANOL® (ENZYME DEVELOPMENT CORPORATION, NEW YORK, N.Y., USA) (0.5%) was added to the reaction mixture and incubated at 50° C. for 60 minutes. The enzymatic-reactions were terminated at 80° C. for 10 minutes. The thus modified rice endosperm protein was filtered through Whatman #0.5 filter paper. The filtrate was subjected to ultrafiltration with a MWCO of 50 kDa Hollow-fiber Polysulfone membrane-cartridge equipped in a Romicon ultrafiltration system (Koch membrane systems, USA) with a capacity of 2-10 L. The solution was ultrafiltrated at a concentration factor of 10 Immediately after ultrafiltration, the residue was diafiltrated two times with twice the volume of deionized water. The resulted residues were spray-dried.

Example 6

Isolation of the Rice Endosperm Protein by Enzymatic Degradation of the Non-Protein Part, Modification of Said Rice Endosperm Protein by Treatment with a Protease and Subsequent Ultra- and Diafiltration of Said Modified Rice Endosperm Protein (REP 6-1 to REP 6-5)

REP 6-1

Enzymatically extracted rice endosperm protein isolate obtained in example 2 (REP 2-1) was subjected to extended hydrolysis by a combined treatment with a serine and a cysteine protease: The protein was mixed with deionized water (1:12.5, w/v), homogenized, adjusted to pH 9.0 and stirred at 60° C. for 10 minutes. The dispersion was treated with food grade ALKALASE® (NOVO NORDISK BIOCHEM, FRANKLINTON, N.C., USA) 2.4 L (0.5%) and incubated at 60° C. for 60 minutes. Then the LIQUIPANOL® (ENZYME DEVELOPMENT CORPORATION, NEW YORK, N.Y., USA) (0.5%) was added to the reaction mixture and incubated at 50° C. for 90 minutes. The enzymatic-reactions were terminated at 80° C. for 10 minutes. The hydrolyate was centrifuged at low speed (1000 g for 10 minutes) to separate insoluble proteins and impurities. The soluble portion of the modified rice endosperm protein were filtered through Whatman #0.4 filter paper and subjected to ultrafiltration with a MWCO of 50 kDa. The solution was ultrafiltrated at a concentration factor of 10 Immediately after ultrafiltration, the retenate was diafiltrated two times with twice the volume of deionized water. During the process of enzymatic hydrolysis, centrifugation, and in ultrafiltration the pH of the (modified) rice endosperm protein was maintained at 8.0 in order to keep the protein soluble. The resulting retentates were spray-dried (REP 6-1).

Detailed Description for Preparation of REP 6-2

Enzymatically extracted rice endosperm protein isolate obtained in example 2 (REP 2-2) was subjected to ALKALASE® (NOVO NORDISK BIOCHEM, FRANKLINTON, N.C., USA) treatment. The protein isolate was mixed with DI water (4%), homogenized, adjusted to pH 9.0 and stirred at 50° C. for 10 min. The dispersion was treated with ALKALASE® (NOVO NORDISK BIOCHEM, FRANKLINTON, N.C., USA) 2.4 L (1%) and the mixture was incubated at 50° C. for 8 min. The enzymatic-reactions were terminated at 70° C. for at pH 5.0 for 15 min. The hydrolysate was centrifuged at low speed (1000 rpm, 1 min) to remove insoluble proteins and impurities. The soluble portion of the hydrolysates was subjected to ultrafiltration with 10 kDa MWCO membrane. The solution was ultrafiltrated to a concentration factor of 5. The resulted retentate (≥10 kDa) was spray-dried and stored at 5° C. (REP 6-2).

Detailed Description for Preparation of REP 6-3

Enzymatically extracted rice endosperm protein isolate obtained in example 2 (REP 2-2) was subjected to ALKALASE® (NOVO NORDISK BIOCHEM, FRANKLINTON, N.C., USA) treatment. The protein isolate was mixed with DI water (4%), homogenized, adjusted to pH 9.0 and stirred at 50° C. for 10 min. The dispersion was treated with ALKA- LASE® (NOVO NORDISK BIOCHEM, FRANKLINTON, N.C., USA) 2.4 L (1%) and the mixture was incubated at 50° C. for 12 min. The enzymatic-reactions were terminated at 70° C. for at pH 5.0 for 15 min. The hydrolysate was centrifuged at low speed (1000 rpm, 1 min) to remove insoluble proteins and impurities. The soluble portion of the hydrolysates was subjected ultrafiltration with 10 kDa MWCO membrane. The solution was ultrafiltrated to a concentration factor of 5. The resulted retentate (>10 kDa) was spray-dried and stored at 5° C. (REP 6-3).

Detailed Description for Preparation of REP 6-4

Enzymatically extracted rice endosperm protein isolate obtained in example 2 (REP 2-2) was subjected to ALKALASE® (NOVO NORDISK BIOCHEM, FRANKLINTON, N.C., USA) treatment. The protein isolate was mixed with DI water (4%), added sodium meta-bisufite (20-mg/g protein), homogenized, adjusted to pH 9.0 and stirred at 50° C. for 10 min. The dispersion was treated with ALKALASE® (NOVO NORDISK BIOCHEM, FRANKLINTON, N.C., USA) 2.4 L (1%) and the mixture was incubated at 50° C. for 8 min. The enzymatic-reactions were terminated at 70° C. for at pH 5.0 for 15 min. The hydrolysate was centrifuged at low speed (1000 rpm, 1 min) to remove insoluble proteins and impurities. The soluble portion of the hydrolysates was subjected to ultrafiltration with 10 kDa MWCO membrane. The solution was ultrafiltrated to a concentration factor of 5. The resulted retentate (>10 kDa) was spray-dried and stored at 5° C. (REP 6-4).

Detailed Description for Preparation of REP 6-5

Enzymatically extracted rice endosperm protein isolate obtained in example 2 (REP 2-2) was subjected to ALKALASE® (NOVO NORDISK BIOCHEM, FRANKLINTON, N.C., USA) treatment. The protein isolate was mixed with DI water (4%), added sodium meta-bisufite (10-mg/g protein), homogenized, adjusted to pH 9.0 and stirred at 50° C. for 10 min. The dispersion was treated with ALKALASE® (NOVO NORDISK BIOCHEM, FRANKLINTON, N.C., USA) 2.4 L (1%) and the mixture was incubated at 50° C. for 30 min. The enzymatic-reactions were terminated at 70° C. for at pH 5.0 for 15 min. The hydrolysate was centrifuged at low speed (1000 rpm, 1 min) to remove insoluble proteins and impurities. The soluble portion of the hydrolysates was subjected to ultrafiltration with 10 kDa MWCO membrane. The solution was ultrafiltrated to a concentration factor of 5. The resulted retentate (>10 kDa) was spray-dried and stored at 5° C. (REP 6-5). (C) Pepsin assisted rice protein extraction followed by ultrafiltration Example 7

Modification of the Rice Endosperm Protein by an Acid Protease and Sub-Sequent Ultrafiltration of Said Modified Rice Endosperm Protein (REP 7)

Five hundred grams of rice flour were homogenized with 3 L deionized water (1:6, w/v) in a blender for 5 minutes at room temperature. The slurry was adjusted to pH 2.4 using 3 N HCl, and the suspension was stirred for 30 minutes at 37° C. The slurry was treated with 0.44% pepsin and incubated at 37° C. for 130 minutes. The solubilized modified rice endosperm protein in the solution was separated by centrifugation (5,000 g, 20 minutes). The residual rice flour was mixed with 500 ml deionized water and the soluble portion was separated by centrifugation to extract more from the residue. Proteins in combined supernatants of first and second extractions were subjected to ultrafiltration using a membrane with a MWCO of 50 kDa as described in example 5. The combined UF & DF excluded the small protein fragments and other impurities effectively.

(D) Analytical Methods

Example 8

Determination of the Emulsion Capacity

The emulsion capacity of the (modified) rice endosperm protein was determined according to the method of Gbogouri et al, Journal of Food Science 2004, Vol. 69, Nr. 8, 615, based on oil titration. Dispersions (0.1% w/w, 50 mL, pH 7.0) of the (modified) rice endosperm protein were prepared in deionized water. The protein solution was homogenized with a homogenizer at setting 1 (Virtishear Tempest, The Virtis Co., Gardiner, N.Y., U.S.A.). Corn oil was added into the protein solution with a flow rate of about 17 g/min using a peristaltic pump. The conductivity of the emulsion was recorded continuously by a conductivity-Meter and used as a parameter for the determination of the inversion point of the emulsion. The amount of oil added to the inversion point was used to calculate the emulsifying capacity. The emulsifying capacity is expressed as the ratio of emulsified oil minus the blank over the amount of proteins in sample. The blank was the quantity of oil added before the phase inversion in 50 mL of deionized water.

Alternatively, the emulsion capacity of protein hydrolysates REP 3-6, 3-7, 3-8, 6-2, 6-3, 6-4, 6-5) was determined according to the method of Vuillemard and others based on oil titration. Protein dispersions (0.5% w/w, 40 mL, pH 7.0) were prepared in distilled water. The protein solution was homogenized with homogenizer at setting 6 (Virtishear Tempest, The Virtis Co., Gardiner, N.Y., U.S.A.). Corn oil was added into the protein solution at about 12 g/min flow rate using a pump. The conductivity of the emulsion was recorded continuously by a conductivity-Meter and used as a parameter for the determination of the inversion point of the emulsion. The amount of oil that added up to the inversion point was used to calculate the emulsifying capacity. Emulsifying capacity is expressed as the ratio of emulsified oil minus the blank over the amount of proteins in sample. The blank was the quantity of oil added before the phase inversion in 40 mL distilled water.

Example 9

Determination of the Emulsion Activity

The emulsion activity was determined by the turbidimetric method of Pearce and Kinsella, Journal of Agric Food Chem. 1978, 26:716-722. A mixture of 6 mL of a 0.1% solution of the (modified) rice endosperm protein in 10 mM phosphate buffer of a pH of 7.0 and 2 mL of corn oil was homogenized for 1 minute with a sonicator at setting 6 (Virtishear Tempest, The Virtis Co., Gardiner, N.Y., U.S.A.). 50 microliters of the mixture were transferred into 5 mL of an 0.1% aqueous solution of SDS (w/v) 0 and 10 minutes after the homogenization. The absorbance of the solution at 500 nm was determined with a spectrometer (Shimadzu Model UV-1601, Kyoto, Japan). The absorbance at the time 0 after homogenization is the emulsion activity of the (modified) rice endosperm protein.

Figure 9:
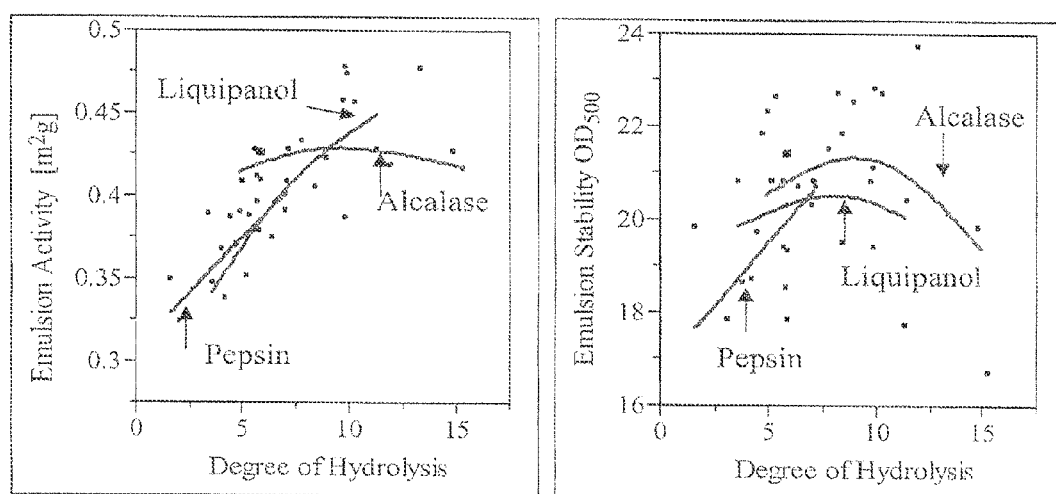
FIG. 9 shows the emulsifying properties of rice protein hydrolysates treated with ALKALASE® (NOVO NORDISK BIOCHEM, FRANKLINTON, N.C., USA), LIQUIPANEOL and pepsin as a function of the degree of hydrolysis.

FIG. 9 shows the emulsifying properties of rice protein hydrolysates treated with ALKALASE® (NOVO NORDISK BIOCHEM, FRANKLINTON, N.C., USA), LIQUI- PANOL® (ENZYME DEVELOPMENT CORPORATION, NEW YORK, N.Y., USA) and Pepsin as a function of the degree of hydrolysis.

Example 10

Determination of the Degree of Hydrolysis

The DH was determined by the method of Nielsen and others (Nielsen, P. M., Petersen, D. & Dambmann, C., 2001. Improved method for determining food protein degree of hydrolysis. Journal of Food Science, 66 (5), 642-646). The o-phthaldialdehyde (OPA) reagent was prepared as follow: 7.620 g of di-sodium tetraborate decahydrate ($Na_2B_4O_7 \cdot 10H_2O$) and 200 mg sodium dodecyl sulfate (SDS) were dissolved in 150 mL of deionized water and then mixed with 160 mg of OPA (97% OPA pre-dissolved in 4 mL of ethanol) and 176 mg of 99% dithiothreitol (DTT). The final solution was made up to 200 mL with deionized water. Freeze dried protein sample of 0.1 g was solubilized in 10 mL deionized water. To measure the absorbance, 3 mL of OPA reagents was added to 10 mL tubes and then 400 μL of sample solution, serine standard (10 mg/100 mL) and deionized water was added in four tubes for each sample, standard and blank, respectively. This was followed by mixing for 5 s and held for exactly 2 min. Absorbance was read at 340 nm with a spectrophotometer (Shimadzu Model UV-1601, Kyoto, Japan). The DH was calculated as follows.

$$DH = h/h_{total} * 100\%;$$

where h is the number of hydrolyzed bonds and $h_{total}$ is the total number of peptide bonds per protein equivalent; h=(Serine-NH2−β)/α equiv/g protein; where h is the number of hydrolyzed bonds and $h_{total}$ is the total number of peptide bonds per protein equivalent; for cereal protein a is 1.00, β is 0.40, and $h_{total}$ is 8.0.

$$Serine\text{-}NH2 = [(A_{340 sample} - A_{340 blank})/(A_{340 standard} - A_{340 blank})] * 0.9516 \text{ meqv/L} * 0.01 * 100/(X*P);$$

where serine-NH2=meqv serine NH2/g protein; X=g sample; P=% protein in sample; 0.01 is the sample volume in liter (L).

Example 11

Determination of the Protein and Total Solubility

Protein solubility was determined by the method of Bera and Mukherjee (Bera, M. B., Mukherjee, R. K. 1989. Solubility, emulsifying, and foaming properties of rice bran protein concentrates. J Food Sci 54(1): 142-145) with some modifications. 200 mg of protein sample was dispersed in 10 mL of deionized water, the pH was adjusted to 7.0 by 1 N HCl or 1 N NaOH. The dispersion was stirred continuously for 30 min and centrifuged at 5000 rpm for 15 min. (model J2-21, Beckman, Fullerton, Calif., U.S.A.). The supernatant was recovered, and the protein content in the supernatant was determined by the Automatic Kjeldahl method (AACC 1990). The percentage of protein solubility was calculated by following equation:

$$\text{Protein Solubility (\%)} = \frac{\text{Protein content of the supernatant}}{\text{Protein in 200 mg protein-isolate}} \times 100$$

The protein solubility was calculated as the percent ratio of protein in the supernatant to that of the total protein in the initial sample.

The total solubility was determined by oven drying method, and expressed as the percent ratio of total soluble portion of the supernatant to that of the total weight of the protein isolate.

$$\text{Total Solubility (\%)} = \frac{\text{Soluble portion of the supernatant}}{200 \text{ mg protein-isolate}} \times 100$$

Figure 6:
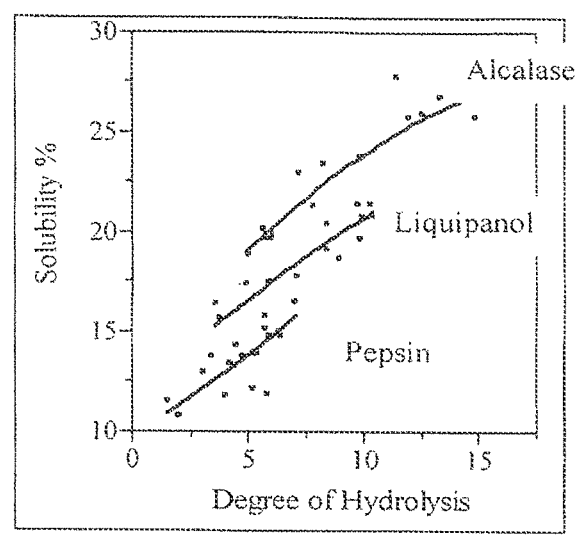
FIG. 6 shows the solubility of the rice endosperm protein hydrolysates treated with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or pepsin as a function of the degree of hydrolysis.

FIG. 6 shows the solubility of the rice endosperm protein hydrolysates treated with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or pepsin as a function of the degree of hydrolysis.

Example 12

Determination of Molecular Weights

The approximate molecular weights of the proteins were determined by SDS-PAGE according to the method of Laemmli, U.K. Cleavage of structural proteins during the assembly of the head of the bacteriophage T4. Nature 1970, 227, 680-686. The SDS-PAGE was carried out on a slab gel (4% stacking gel, 12% separating gel) in an SDS-Tris-Glycine discontinuous buffer system. Protein solutions (6-10 μg protein/μL) were prepared in non-reducing sample buffer (62.5 mM Tris-HCl pH 6.8, 2% SDS, 10% glycerol, and 0.05% bromophenol blue). Twelve microliters of the solutions were loaded onto the gel. Electrophoresis was performed at a constant voltage of 200 V for approximately 40 min. The gel was stained by 0.1% Coomassie brilliant blue in acetic acid/ethanol/water solution (10:40:50, v:v:v) and de-stained in the same solvent without Coomassie brilliant blue. The approximate molecular weights were determined by Bio-Rad broad range molecular weight standards ranging from 6.5 to 200 kDa. Molecular weights and density of bands were determined by using image analysis software, windows Mac & Dos, Advanced American Biotechnology & Biomedical Instruments Inc, CA, USA.

Example 13

Determination of Surface Hydrophobicity

Surface hydrophobicity of the protein isolates was determined by hydrophobic fluorescence probes of 1-anilino-8-naphthalene sulfonate (ANS) from the method outlined by Hayakawa and Nakai, Relationships of hydrophobicity and net charge to the solubility of ilk and soy proteins, J. Food Sci. 1985, 50, 486-491. Four-milliliters of protein solutions were made in 0.01 M phosphate buffer (pH 7) with concentrations ranging from 0.008 to 0.025% w/v. Ten-microliters of 8 mM ANS in 0.01 M phosphate buffer (pH 7) was added into each protein solution and fluorescence intensities of these solutions were measured at 390 nm of excitation and 470 nm of emission with a spectro-fluorophotometer (Shimadzu Model RF-1501, Kyoto, Japan). The surface hydrophobicity, expressed as the slope of fluorescence intensity vs. protein concentration, was calculated by linear regression.

Figure 5:
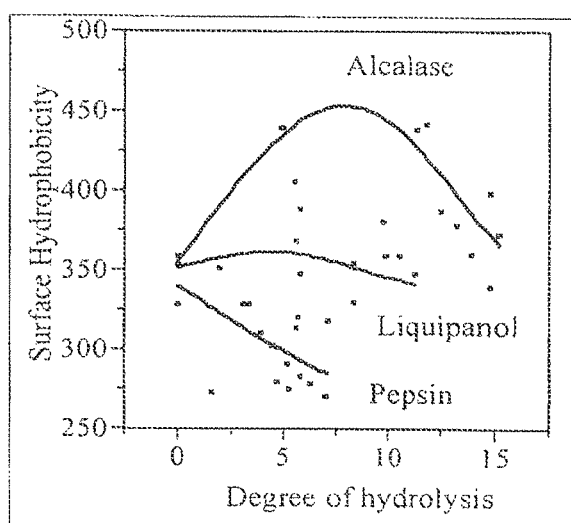
FIG. 5 shows the surface hydrophobicity of the rice endosperm protein hydrolysates treated with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or pepsin as a function of the degree of hydrolysis.

FIG. 5 shows the surface hydrophobicity of the rice endosperm protein hydrolysates treated with ALKALASE® (NOVO NORDISK BIOCHEM, FRANKLINTON, N.C., USA), LIQUIPANOL® (ENZYME DEVELOPMENT CORPORATION, NEW YORK, N.Y., USA) or pepsin as a function of the degree of hydrolysis.

Example 14

Determination of Viscosity

Viscosity of the protein isolates was determined by a rotational rheometer (Haake VT 550, Germany) equipped with a MVDIN measuring spindle (radius=19.36 mm, height=58.08 mm) at room temperature (26° C.). The protein isolates were mixed with deionized water to form slurry of 10%, and the slurry was left for 60 min for equilibrium before analysis. The samples (30 ml) were loaded into the cylindrical cup (radius=21.0 mm) and were subjected to a shear rate that changed from 0 to 400 l/s over 3 min using a computer-controlled program. The data were analyzed by Rheowin Pro Data manager version 2.84 (Haake Mess Tech, Germany).

Example 15

Determination of Thermal Properties

Thermal properties were determined using a differential scanning calorimeter model Pyris-1 (Perkins-Elmer Corp., Norwalk, Conn., U.S.A.) equipped with thermal analysis software (Version 4.00, Pyris-1-DSC, Perkin-Elmer Corp., Norwalk, Conn., U.S.A.). Two-hundred milligrams of protein were dispersed in an appropriate amount of water to form slurry with a protein content of 20%. The slurry was well mixed and left for 60 min for equilibrium before analysis. The slurry (about 50 µL) was weighed accurately into stainless steel pan (large volume capsule), hermetically sealed, and scanned during temperature increasing from 25 to 140° C. at a rate of 10° C./min. An empty pan was used as a reference. Peak temperature and enthalpy were computed from thermogram using the data processing software.

Emulsifying activity and stability were determined by the turbidimetric method of Pearce and Kinsella using the procedure of Example 9. Absorbance at time 0 was expressed as the emulsifying activity of rice endosperm protein and emulsion stability (ES) was calculated as follows:

Emulsion Stability=$T_0 \times \Delta t / \Delta T$ where, $\Delta T$ is the decrease in turbidity (absorbance) of the initial absorbance (To) during the time interval of $\Delta t$ (10 min)

All the experiments were done in triplicates. Data were analyzed for variance and multiple mean comparisons with JMP 5.1 software (SAS Inst) SAS, 2002, JMP® User's Guide, Version 5. SAS Institute Inc., Cary, N.C. The significance of difference between means was determined by the Tukey HSD procedure at the 5% significance level (P<0.05).
(E) Results In the following Table 3a the emulsion activity and capacity of the (modified) rice endosperm proteins (REP 1-1 to REP 7) obtained according to examples 1 to 7 measured by the methods as described in example 9 and 8, respectively, are given.

For REP 3 eight values are given, because the example was carried out eight times, each time with another of the following enzymes: BROMELAIN, PROTEX 6L, pepsin, ALKALASE® (NOVO NORDISK BIOCHEM, FRANKLINTON, N.C., USA) or LIQUIPANOL® (ENZYME DEVELOPMENT CORPORATION, NEW YORK, N.Y., USA) (see REP 3-1 to REP 3-8), and for REP 6 five values are given, because the example was carried out five times (see REP 6-1 to REP 6-5), each time applying different process conditions as described in detail in example 6.

TABLE 3a

Emulsion activity and capacity of the (modified) rice endosperm proteins REP 1-1 to REP 7 according to examples 1 to 7

| (Modified) rice endosperm protein | Emulsion activity | Emulsion capacity [ml/g protein] |
|---|---|---|
| REP 1-1 | 0.221 | 228.1 |
| REP 2-1 | 0.214 | 177.6 |
| REP 3-1 (Bromelain) | 0.469 | 283.7 |
| REP 3-2 (Protex 6L) | 0.507 | 346.5 |
| REP 3-3 (Pepsin) | 0.584 | 363.8 |
| REP 3-4 (ALKALASE ® (Novo Nordisk Biochem, Franklinton, NC, USA)) | 0.527 | 357.1 |
| REP 3-5 (LIQUIPANOL ® (Enzyme Development Corporation, New York, NY, USA)) | 0.578 | 386.8 |
| REP 3-6 | 0.409 | 477.5 |
| REP 3-7 | 0.361 | 426.7 |
| REP 3-8 | 0.370 | 439.1 |
| REP 4 | 0.624 | 467.8 |
| REP 5 | 0.643 | 541.7 |
| REP 6-1 | 0.604 | 581.5 |
| REP 6-2 | 0.341 | 388.9 |
| REP 6-3 | 0.342 | 421.5 |
| REP 6-4 | 0.365 | 436.8 |
| REP 6-5 | 0.277 | 341.5 |
| REP 7 | 0.473 | 228.7 |

In the following tables 3b and 3c the protein and total solubility and the degree of hydrolysis of the modified rice endosperm proteins REP 3 and 6 obtained according to examples 3 and 6 measured by the methods as described in example 10 and 11, respectively, are given.

TABLE 3b

Protein and total solubility of the modified rice endosperm proteins REP 3 and REP 6 according to examples 3 and 6

| Modified rice endosperm protein | Protein solubility (%) | Total solubility (%) |
|---|---|---|
| REP 3-6 | 31.1 | 45.0 |
| REP 3-7 | 34.7 | 49.5 |
| REP 3-8 | 36.9 | 53.0 |
| REP 6-2 | 29.4 | 47.2 |
| REP 6-3 | 33.3 | 56.4 |
| REP 6-4 | 32.8 | 49.7 |
| REP 6-5 | 38.3 | 58.2 |

TABLE 3c

Degree of hydrolysis of the modified rice endosperm proteins REP 3 and REP 6 according to examples 3 and 6

| Modified rice endosperm protein | *Degree of hydrolysis (DH) | **Degree of hydrolysis (DH) |
|---|---|---|
| REP 3-6 | 3.7 | — |
| REP 3-7 | 4.3 | — |
| REP 3-8 | 5.9 | — |
| REP 6-2 | 3.4 | 5.6 |
| REP 6-3 | 4.6 | 6.7 |
| REP 6-4 | 3.8 | 5.1 |
| REP 6-5 | 6.7 | 8.8 |

*DH - enzymatic hydrolysis (before centrifugation and ultrafiltration)
**DH of the final products (enzymatic hydrolysis, after centrifugation and ultrafiltration)

An overview of the chemical and enzymatic extraction procedures are presented in FIGS. 1 and 2, respectively. Of the total protein in rice flour, alkali- and salt-methods extracted protein isolates of 87.2 and 89.4% protein content, with 67.9 and 60.3% yield, respectively. In alkali and salt methods, the pH had strong influence on protein extraction. A positive correlation of pH and the extractability were found up to pH 12. However, high pH could lead to undesirable protein modification and increased the extraction of non-protein components that co-precipitate with protein and lower the isolate quality. However, the pH 10 or below was a poor solvent for rice protein extraction. Therefore, pH 11 was determined to be the optimum extraction pH concerning protein yield. Regarding protein functionality—such as emulsifying properties of the protein—a lower pH (preferably pH 8 to 10) might be of interest. Further, protein extraction at pH 11 combined with pretreatment of 3 min homogenization or sonication improved the extractability of the protein. These pretreatments might have dissociated the hydrophobically interacted protein-protein or protein-polysaccharide interactions and facilitated the protein extraction.

In enzyme extraction, the thermo stable alpha amylase, TERMAMYL, followed by cellulase treatment isolated 85.8% protein content with 89.2% yield. The enzyme TERMAMYL has optimum activity at 90° C. In order to avoid extensive protein denaturation at 90° C. during TERMAMYL treatment, the procedure was adapted with another non-thermo stable amylase (amylase S), with optimum activity at 70° C. The amylase S combined with cellulase treatments isolated 81.7% protein with 90.5% yield as shown in the table below:

TABLE 4

Protein Content and Recovery of Rice Protein Isolates with Optimized Conditions[a]

| Rice protein isolates | Protein (%) | Protein recovery (%) |
|---|---|---|
| REP 1-3: $RP_A$ (Alkali) | 87.2 ± 1.08 | 67.9 ± 3.37 |
| REP 1-4: $RP_S$ (Salt) | 89.4 ± 1.96 | 60.3 ± 2.18 |
| REP 2-3: $RP_{ET}$ (Termamyl) | 85.8 ± 1.12 | 89.2 ± 2.31 |
| REP 2-4: $RP_{EA}$ (Amylase S) | 81.7 ± 1.18 | 90.5 ± 1.36 |

[a]Values are means of triplicate determination and on dry weight basis.

The compositions of the rice proteins, albumin, globulin, glutelin and prolamin are presented in Table 4. Rice flour contained 7.8% protein with 4.1%, albumin, 11.8% globulin, 77.4% glutelin, and 2.1% prolamin of the total protein. Alkali and salt extraction had similar profiles of proteins except globulin; salt-extracted protein contained higher globulin (6.2%) than alkali-extracted protein (3.1%). Since the major protein in rice is glutelin, the alkali- and salt-extracted proteins contained higher percentages of glutelin, 87.9 and 86.7, respectively, than the enzyme extracted proteins (80.2%). In contrast, prolamin content is higher in enzyme-extraction (2.8%) than in alkaline- (0.5%) and salt- (0.7%) extractions.

TABLE 5

Albumin, Globulin, Glutelin, and Prolamin Content of Chemical- and Enzyme-Extracted Protein Isolates[a]

| | | % of total protein | | | |
|---|---|---|---|---|---|
| Protein fraction components (%) | Rice flour | REP 1-3: $RP_A$ Alkali | REP 1-4: $RP_S$ Salt | REP 2-3: $RP_{ET}$ Termamyl | REP 2-4: $RP_{EA}$ Amylase S |
| Total protein | 7.92 | 87.2 ± 1.1 | 89.4 ± 1.2 | 85.8 ± 1.1 | 81.7 ± 1.0 |
| Albumin | 4.13 | 2.9 ± 0.1 | 2.6 ± 0.2 | 1.7 ± 0.1 | 1.8 ± 0.1 |
| Globulin | 11.88 | 3.8 ± 0.2 | 6.2 ± 0.3 | 7.7 ± 0.0 | 7.1 ± 0.6 |
| Glutelin | 77.43 | 87.2 ± 1.1 | 86.7 ± 0.9 | 80.6 ± 0.7 | 81.1 ± 1.05 |
| Prolamin | 2.06 | 1.5 ± 0.4 | 1.1 ± 0.1 | 2.8 ± 0.1 | 2.9 ± 0.1 |
| Non-extractable | 4.3 | 3.1 ± 0.6 | 2.9 ± 0.1 | 6.4 ± 0.6 | 5.7 ± 0.4 |

[a]Values are means of triplicate determination.

The composition of the four protein isolates are shown in Table 6. Both RPA and $RP_S$ had similar composition and both of them had higher protein content, 87.2 and 89.4%, respectively, than those of enzymes-extracted proteins, $RP_{ET}$ (84.8%), and $RP_{EA}$ (81.7%). The non-protein components including starch, lipid, fiber, ash were lower in both alkali- and salt-extracted proteins than in enzyme-extracted proteins.

TABLE 6

Proximate Composition of Rice Protein Isolates[a] REP 1-3, 1-4, 2-3 and 2-4

| Proximate composition (%) | REP 1-3: $RP_A$ Alkali | REP 1-4: $RP_S$ Salt | REP 2-3: $RP_{ET}$ Termamyl | REP 2-4: $RP_{EA}$ Amylase S |
|---|---|---|---|---|
| Moisture | 2.4 ± 0.23[a] | 2.5 ± 0.09[a] | 2.0 ± 0.11[a] | 2.3 ± 0.07[a] |
| Protein | 87.2 ± 1.08[ab] | 89.4 ± 1.96[a] | 85.8 ± 1.12[b] | 81.7 ± 1.08[c] |
| Starch | 2.1 ± 0.48[c] | 1.7 ± 0.61[c] | 5.1 ± 0.38[b] | 6.7 ± 0.47[a] |
| Lipid | 0.3 ± 0.04[b] | 0.2 ± 0.06[b] | 1.1 ± 0.05[a] | 1.1 ± 0.13[a] |
| Fiber | 0.6 ± 0.43[b] | 0.5 ± 0.17[b] | 4.8 ± 0.46[a] | 5.3 ± 0.51[a] |
| Ash | 0.4 ± 0.07[b] | 0.7 ± 0.04[b] | 3.7 ± 0.13[a] | 3.4 ± 0.09[a] |

[a]Values are means of triplicate determination and on dry weight basis. Mean values with different letters in the same row are significantly different (P < 0.05).

Figure 3:
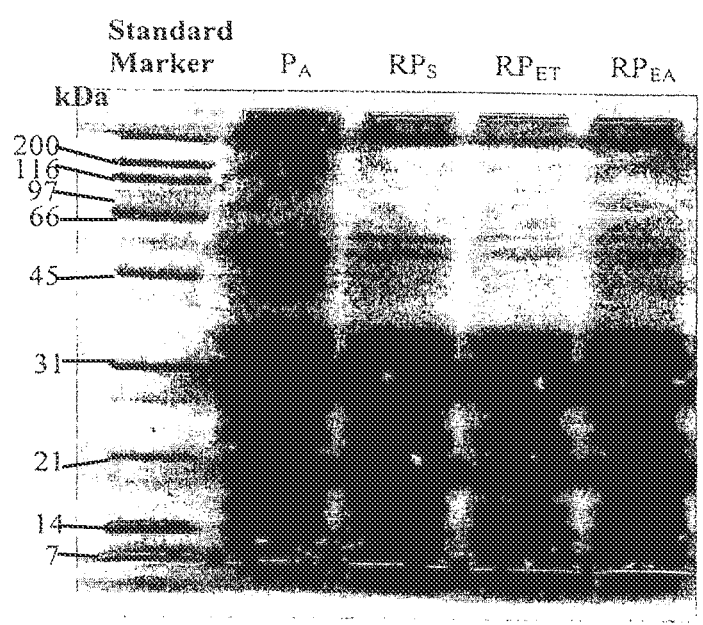
FIG. 3 shows the electrophoresis profiles of the rice protein isolates of Table 6.

Electrophoresis profiles of rice proteins are shown in FIG. 3.

Molecular size profiles of rice proteins determined by SDS PAGE gel electrophoresis
Lane 1—Standard marker (6.5-200 kDa);
Lane 2—RPA;
Lane 3—$RP_S$;
Lane 4—$RP_{ET}$;
Lane 5—$RP_{EA}$.

Rice protein had a total of 6 bands and the molecular size ranged from 7 to 97 kDa. Major bands were observed at 97 kDa (2%), 45 kDa (3%), 33 kDa (72%), 21 kDa (7%), 14 kDa (6%), and 7 kDa (8%). The most predominant band was observed at the molecular size of 33 kDa with the density of 72% (FIG. 3, lanes 1 and 2). This is the major rice protein, glutelin.

The thermal denaturation temperature and enthalpy values of denaturation of the rice protein isolates are presented in Table 7.

TABLE 7

Thermal Properties of Rice Protein Isolates REP 1-3, 1-4, 2-3 and 2-4 and Rice Flour[a]

| Rice protein Isolates | Denaturation temperature (° C.) | Enthalpy value of Denaturation ($Jg^{-1}$) |
|---|---|---|
| REP 1-3: $RP_A$ (Alkali) | 81.4 ± 1.1[a] | 1.82 ± 0.14[b] |
| REP 1-4: $RP_S$ (Salt)) | 78.9 ± 1.8[ab] | 1.10 ± 0.09[c] |
| REP 2-3: $RP_{ET}$ (Termamyl) | nd | Nd |
| REP 2-4: $RP_{EA}$ (Amylase S) | 79.9 ± 2.1[b] | 0.18 ± 0.06[d] |
| Rice flour | 78.8 ± 2.7[ab] | 7.31 ± 0.19[a] |

[a]Values are means of triplicate determination. Mean values with different letters in the same column are significantly different (P < 0.05).
*nd, non-detectable.

The denaturation temperatures of RPA, $RP_S$, $RP_{ET}$, and $RP_{EA}$ were 81.4, 78.9, 79.9, and 78.8° C., respectively. Enthalpy values of RPA (1.82 J/g), $RP_S$ (1.10 J/g), $RP_{ET}$ (non-detectable), and $RP_{EA}$ (0.18 J/g) differed significantly, indicating that the extraction methods denatured the proteins at varying degrees depending on extraction conditions. The enthalpy changes could be used to predict the extent of protein denaturation. Biliaderis, C. G., Differential scanning calorimetry in food research: A review Food Chem. 1983, 10, 239-265. The enthalpy change is decreased when the protein is partially denatured, and the enthalpy change is zero when the protein is completely denatured. Yu, Z. Y., Hettiarachchy, N. S.; Rath, N., Extraction, denaturation and hydrophobic properties of rice flour proteins, J. Food Sci. 2001, 66 (2), 229-232, reported that the enthalpy values of 2.88, 3.14, and 3.79 J/g for albumin, globulin, and glutelin, respectively. In our study, alkali-extracted protein (RPA) had the highest enthalpy value (1.82 J/g), which was significantly lower than the values of Yu et al for albumin (2.88 J/g), globulin (3.14 J/g), and glutelin (3.79 J/g). The physical treatments applied in alkali and salt extraction may have denatured the protein to a degree. Among the enzyme-extracted proteins, $RP_{ET}$ (TERMAMYL, at 90° C.) did not show any detectable enthalpy changes, which indicated complete protein denaturation.

Surface Hydrophobicity and Solubility

The surface hydrophobicity, solubility, and viscosity of the rice protein isolates are presented in Table 8.

TABLE 8

Surface Hydrophobicity, Solubility, and Viscosity of Rice Protein Isolates[a] REP 1-3, 1-4, 2-3 and 2-4

| | REP 1-3: $RP_A$ (Alkali) | REP 1-4: $RP_S$ (Salt) | REP 2-3: $RP_{ET}$ (Termamyl) | REP 2-4: $RP_{EA}$ (Amylase S) |
|---|---|---|---|---|
| Surface hydrophobicity | 563.8 ± 14.8[c] | 544.2 ± 13.1[c] | 931.3 ± 15.6[a] | 771.6 ± 12.3[b] |
| Solubility % (at pH 7.0) | 13.6 ± 1.6[a] | 11.6 ± 1.5[a] | 8.1 ± 1.1[b] | 9.3 ± 2.0[b] |
| Viscosity Pas (10%, w/v) | 17.4 ± 0.6[a] | 17.2 ± 0.9[a] | 17.0 ± 1.1[a] | 18.2 ± 1.4[a] |
| pH | 7.0 ± 0.2 | 6.8 ± 0.6 | 6.8 ± 0.2 | 6.9 ± 0.3 |

[a]Values are means of triplicate determination. Mean values with different letters in the same row are significantly different (P < 0.05).

Hydrophobicity of rice protein isolates ranged from 544 to 931. The method of extraction contributed to the differences in hydrophobicities of these proteins. The hydrophobicity of enzyme-extracted proteins, $RP_{ET}$ (931.3) and $RP_{EA}$ (791.6), were higher than that of alkali- and salt-extracted proteins, which were 563.8 and 544.2, respectively. This might be due to protein denaturation, which increased surface hydrophobicity. The heat-induced unfolding of enzyme-extracted proteins increased surface hydrophobicity.

The solubility of rice protein isolates were low at a wide pH range of 4 to 10 (Data not shown). Amino acid composition and hydrophobic interactions determine solubility. Sub-fractionation studies of rice glutelin by Tecson et al (8) showed that high molecular mass of rice glutelin had excessive intra- and inter-molecular disulfide and hydrophobic interactions, which reduced its solubility. Wen and Luthe (9) also reported that the most abundant amino acids in rice glutelin are glutamic acid/glutamine, aspartic acid/asparagine, arginine, glycine, and alanine. The amide groups in the glutamine and asparagine side chains promoted the aggregation of glutelin and reduced the rice protein solubility. Comparatively, the enzyme-extracted proteins had lower solubility than the alkali- and salt-extracted proteins, which might be due to the high level of denaturation, high surface hydrophobicity, and loss of water-soluble protein (albumin) in extraction.

The emulsifying and foaming properties of rice protein isolates are presented in Table 9.

TABLE 9

Emulsifying and Foaming Properties of Rice Protein Isolates[a]

|  | REP 1-3: $RP_A$ (Alkali) | REP 1-4: $RP_S$ (Salt) | REP 2-3: $RP_{ET}$ (Termamyl) | REP 2-4: $RP_{EA}$ (Amylase S) |
|---|---|---|---|---|
| Emulsifying activity | $0.244 \pm 0.11^a$ | $0.215 \pm 0.01^a$ | $0.146 \pm 0.07^b$ | $0.176 \pm 0.21^b$ |
| Emulsifying stability (min) | $19.6 \pm 0.91^a$ | $17.1 \pm .81^b$ | $13.2 \pm 2.11^c$ | $14.7 \pm 0.91^c$ |
| Foaming capacity (ml) | $12.6 \pm 1.2^a$ | $13.5 \pm 1.0^a$ | $8.4 \pm 0.8^b$ | $9.1 \pm 0.7^b$ |
| Foaming stability (min) | $8.6 \pm 0.9^a$ | $8.2 \pm 0.6^a$ | $5.3 \pm 0.4^b$ | $6.8 \pm 0.9^b$ |

[a]Values are means of triplicate determination. Mean values with different letters in the same row are significantly different (P < 0.05).

The emulsifying and foaming properties of alkali- and salt-extracted proteins were higher than those of enzyme-extracted proteins. Emulsifying activities of alkali- and salt-extracted proteins were 0.224 and 0.216, respectively, and stabilities were 19.6 and 17.1 min, respectively, which were significantly higher than those of enzyme-extracted proteins. A similar pattern of results was observed in foaming capacity and stabilities. To have emulsifying and foaming properties, the protein should be able to solubilize in the aqueous phase and rapidly unfold to form a cohesive layer at the interface. The molecular and physical requirements of proteins to stabilize emulsion and foam are similar (Damodarn, S., Protein-stabilized foams and emulsions, J. Food Sci. 205, 70 (3), 54-66).

The possible reasons for the differences in functional properties obtained by the different methods of extraction could be due to protein purity, composition, surface hydrophobicity, and solubility of the protein isolates. However, it is not meant, that the applicant is bound by these theories.

Firstly, the thermal properties of the two enzyme-extracted proteins showed a higher degree of denaturation than those of $RP_A$ and $RP_S$. Excessive denaturation could be detrimental to emulsifying and foaming properties by either promoting protein aggregation or exposing a greater number of hydrophobic amino acids. The surface hydrophobicity data confirmed the increased hydrophobicity of enzyme-extracted proteins. The excessive surface hydrophobicity may be unfavorable for emulsifying or foaming properties of protein by facilitating to form extensive hydrophobic bonding and reduced solubility and flexibility of the protein.

Secondly, the extreme extraction conditions such as high temperature and or pH might have promoted the formation of disulfide cross-linking. It has been reported that rice glutelin has excessive disulphide linkages. Extremely low solubility of the extracted protein indicated that heat- or pH-induced unfolding of the protein during extraction might have exposed thiol groups in the interior of the protein. These exposed thiol groups could readily form disulfide linkages with adjacent protein molecules. The newly formed disulfide bonds might have reduced the molecular flexibility, solubility, and surface activity of the proteins. The flexibility of a certain segments of a protein is one of the major properties determining the emulsifying and foaming properties of a protein.

Thirdly, the composition of rice protein isolates showed that alkali- and salt-extracted protein isolates contained higher amounts of proteins and lower amounts of non-protein substances than those of enzyme-extracted proteins. Significant amounts of fiber, ash, lipid, and residual starch in the enzyme extracted protein isolates, $RP_{ET}$ and $RP_{EA}$, might have reduced their emulsifying and foaming properties. These non-protein components may interact with proteins and modify the net charge and hydrophobicity of proteins, affecting the protein functionalities.

Finally, lower solubility of the enzyme extracted protein adversely affected the emulsifying and foaming properties. To have emulsion and foaming properties, the proteins should be able to solubilize and unfold to form cohesive layers at the interface. This requires protein solubility and flexibility. Lacking these properties, the enzyme-extracted proteins had diminished emulsifying and foaming properties than the alkali- and salt-extracted proteins.

From these investigations it has been found that alkali and salt methods extracted 87.2 and 89.4% of proteins with 67.9 and 60.3% yield respectively. Enzymatic method with TERMAMYL and amylase S extracted 84.8 and 81.8% proteins with 89.2 and 90.5% yield, respectively. The alkali- and salt-extracted proteins had higher protein contents and lower non-protein components including starch, lipid, fiber, and ash than the enzyme-extracted proteins. Comparatively, more favorable protein composition, lower hydrophobicity, higher solubility, and a lower degree of thermal denaturation of alkali- and salt-extracted proteins contributed to higher emulsifying and foaming properties than those of enzyme-extracted proteins. Therefore, the alkali and salt method of extractions were milder extraction conditions and the proteins retained better functional properties.

Rice proteins are nutritional and hypoallergenic, and healthy for human consumption. Efficient extraction with approved food grade enzymes and chemicals are essential for commercial production and application of rice protein as a functional ingredient. Rice endosperm proteins were isolated by alkali, salt, and enzymatic methods and evaluated for extractability and physicochemical properties. Alkali (RPA) and salt ($RP_S$) methods extracted 87.2 and 89.4% of proteins with 67.9 and 60.3% yield, respectively. The enzymatic methods with TERMAMYL ($RP_{ET}$) and amylase S ($RP_{EA}$) extracted 84.8 and 81.8% proteins with 89.2 and 90.5% yield, respectively. Enthalpy values of RPA (1.82 J/g), $RP_S$ (1.10 J/g), $RP_{ET}$ (non-detectable), and $RP_{EA}$ (0.18 J/g) determined by Differential Scanning calorimeter, demonstrated that the varying level of denaturation of proteins depends on the method of extraction. Surface hydrophobicity data supported this observation. Alkali- and salt-extracted proteins had higher solubility and emulsifying properties than those of enzyme-extracted proteins; therefore, alkali- and salt-extracted proteins can have enhanced functional use and a potential starting material for preparing tailored rice protein isolates.

Rice endosperm protein isolated with a thermo-stable alpha-amylase, TERMAMYL, was treated with neutral, acid, and/or alkaline proteases. The degree of hydrolysis of the hydrolysates was optimized by OPA method to maximize the solubility and emulsifying properties. After enzyme inactivation, the soluble fraction was separated by centrifugation (1000 g for 10 min), and the soluble hydrolysate was filtered through membrane of specific molecular weight cut-off (50 kDa). The resulted hydrolysate of greater than 50 kDa was spray dried and evaluated for degree of hydrolysis, solubility, emulsion capacity, activity, and stability.

The combined treatments of two types of proteases; Cysteine (LIQUIPANOL® (ENZYME DEVELOPMENT CORPORATION, NEW YORK, N.Y., USA)) and serine (ALKALASE® (NOVO NORDISK BIOCHEM, FRANKLINTON, N.C., USA)) proteases followed by centrifugation and ultrafiltration significantly improved solubility and emulsifying properties. The resulted hydrolysate had 53.5% solubility; 586.3 ml/g emulsion-capacity, 0.604-activity, and 24.8 min-stability, which were significantly higher than that of unmodified rice protein isolate (solubility 11.8%, 177.6 ml/g emulsion-capacity, 0.214 activity, and, 14.7 min-stability).

The combined enzymatic hydrolysis with ALKALASE® (NOVO NORDISK BIOCHEM, FRANKLINTON, N.C., USA) and LIQUIPANOL® (ENZYME DEVELOPMENT CORPORATION, NEW YORK, N.Y., USA) followed by ultrafiltration improved rice endosperm protein solubility and emulsifying properties. The ultrafiltrated rice endosperm protein hydrolysate with uniform molecular fractions of high-purity enhanced its solubility and emulsifying properties.

Example 12

Manufacture of a formulation of β-carotene

A formulation comprising a rice endosperm protein and β-carotene may be prepared as follows:

a) Preparation of a(n Oil-Based) Solution 1:

7.7 g of corn oil and 1.4 g of dl-α-tocopherol were mixed. 16.1 g of crystalline β-carotene were dispersed in 180 ml of chloroform (trichloromethane) and the resulting dispersion was added to the mixture of corn oil and tocopherol. By gently stirring and simultaneous heating the mixture to about 60° C. a solution was obtained.

b) Preparation of a(n Aqueous) Solution 2:

35 g of REP 1 (REP 1-1) according to example 1 was re-dissolved in 250 ml of water by stirring at 60° C. Alternatively REP 1-1 freshly prepared according to example 1 could be used, i.e. the steps of freeze drying and storing are not carried out, but the resulting REP 1-1 solution is used as such, and brought to a temperature of 60° C. Additionally 2.1 g of ascorbyl palmitate and 42.7 g of sucrose were added. 8 ml of aqueous 1 N NaOH were used to adjust the pH to a value of 7.9. Instead of REP 1-1, REP 1-2 can be used accordingly for the preparation of the aqueous solution.

c) Preparation of an Emulsion from the Solutions 1 and 2:

Under vigorous stirring solution 1 was added to solution 2 at 53° C. and the dispersion was vigorously stirred for another 30 minutes. The stirred dispersion was kept at 50 to 55° C. for 30 minutes. Residual trichloromethane was removed at 50 to 55° C. After removing entrapped air bubbles by centrifugation the emulsion was gently stirred at 50 to 55° C. for some minutes and then characterised with respect to the particle size of the inner phase. The mean particle size (Sauter diameter, D[3, 2]) of the inner phase of the emulsion was 380 nm as measured by laser diffraction (Malvern Masersizer).

d) Preparation of a Solid Formulation from the Emulsion:

The emulsion may be sprayed into a pre-cooled fluidised bed of cornstarch. Excess cornstarch can be removed by sieving and the powder obtained can be dried in an air stream at room temperature. The powder particle fraction in the range of 0.16 to 0.50 mm can be collected by sieving and characterised with respect to the carotenoid content, the colour intensity and the colour hue in an aqueous dispersion, the content of the corn starch and residual humidity.

TABLE 10

| Calculated composition of the dried formulation | |
|---|---|
| Compound | Amount [weight-%, based on the total dry weight] |
| REP 1-1: Rice endosperm protein according to example 1 | 25.0 |
| sucrose | 30.5 |
| ascorbyl palmitate | 1.5 |
| β-carotene | 11.5 |
| corn oil | 5.5 |
| dl-α-tocopherol | 1.0 |
| Corn starch fluid | 25.0 |

The invention claimed is:

1. A process for preparing a composition comprising a rice endosperm protein and an active ingredient which process comprises the following steps:
   I) preparing an aqueous solution or colloidal solution of said rice endosperm protein,
   II) preparing a solution or dispersion of an active ingredient, wherein said active ingredient is a fat-soluble active ingredient and/or colorant, and optionally comprises at least a fat-soluble adjuvant and/or excipient,
   III) mixing the solutions prepared in step I) and step II),
   IV) homogenizing the mixture resulted from step III,
   V) submitting the mixture after having performed step IV) to enzymatic treatment in order to cross-link the rice endosperm protein.

2. The process according to claim 1, wherein the enzymatic treatment according to step V) uses a cross-linking enzyme that is transglutaminase.

* * * * *